US011918767B2

(12) United States Patent
Howell et al.

(10) Patent No.: US 11,918,767 B2
(45) Date of Patent: Mar. 5, 2024

(54) RAPIDLY INSERTABLE CENTRAL CATHETERS INCLUDING CATHETER ASSEMBLIES AND METHODS THEREOF

(71) Applicant: Bard Access Systems, Inc., Salt Lake City, UT (US)

(72) Inventors: Glade H. Howell, Draper, UT (US); Jason R. Stats, Layton, UT (US); Huy Ngoc Tran, Riverton, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 38 days.

(21) Appl. No.: 17/237,909

(22) Filed: Apr. 22, 2021

(65) Prior Publication Data

US 2021/0330941 A1    Oct. 28, 2021

Related U.S. Application Data

(60) Provisional application No. 63/014,555, filed on Apr. 23, 2020.

(51) Int. Cl.
  *A61M 25/06* (2006.01)
  *A61M 25/00* (2006.01)
  (Continued)

(52) U.S. Cl.
  CPC .... *A61M 25/0631* (2013.01); *A61M 25/0026* (2013.01); *A61M 25/007* (2013.01);
  (Continued)

(58) Field of Classification Search
  CPC .......... A61M 25/0631; A61M 25/0026; A61M 25/007; A61M 25/09; A61M 2025/024;
  (Continued)

(56) References Cited

U.S. PATENT DOCUMENTS 1,013,691 A    1/1912   Shields
3,225,762 A    12/1965  Guttman
              (Continued)

FOREIGN PATENT DOCUMENTS

DE    202012006191 U1    7/2012
EP        0653220 A1      5/1995
              (Continued)

OTHER PUBLICATIONS

PCT/US2020/048583 filed Aug. 28, 2020 International Search Report and Written Opinion dated Nov. 13, 2020.
(Continued)

*Primary Examiner* — Brandy S Lee
*Assistant Examiner* — Fatimata Sahra Diop
(74) *Attorney, Agent, or Firm* — Rutan & Tucker LLP

(57) ABSTRACT

Rapidly insertable central catheters ("RICCs") including catheter assemblies and methods thereof are disclosed. A RICC assembly can include a RICC, an introducer, and a coupling system configured to couple the RICC and the introducer together. A catheter tube of the RICC includes a side aperture in a distal-end portion of the catheter tube, which opens into an introducing lumen extending from the side aperture to a distal end of the RICC. The introducer includes a syringe and an introducer needle having a cannula. The coupling system includes a distal coupler slidably attached to the catheter tube proximal of the side aperture. The cannula extends through a longitudinal through hole of the distal coupler, through the side aperture of the catheter tube, along the introducing lumen of the catheter tube, and through the distal end of the RICC when the RICC assembly is in at least a ready-to-deploy state thereof.

25 Claims, 9 Drawing Sheets

(51) Int. Cl.
*A61M 25/09* (2006.01)
*A61M 25/02* (2006.01)

(52) U.S. Cl.
CPC ....... *A61M 25/09* (2013.01); *A61M 2025/024* (2013.01); *A61M 2210/125* (2013.01)

(58) Field of Classification Search
CPC ........ A61M 2210/125; A61M 25/0069; A61M 25/0097; A61M 25/06; A61M 25/0693; A61M 25/09041; A61M 25/0111; A61M 25/0043; A61M 25/0068; A61M 25/0102; A61M 25/0113; A61M 25/065; A61M 2025/0063; A61M 25/0606; A61M 25/0029; A61M 2025/0002; A61M 2205/0216
See application file for complete search history.

(56) References Cited

U.S. PATENT DOCUMENTS

| | | | |
|---|---|---|---|
| 3,382,872 | A | 5/1968 | Rubin |
| 3,570,485 | A | 3/1971 | Reilly |
| 3,890,976 | A | 6/1975 | Bazell et al. |
| 4,205,675 | A | 6/1980 | Vaillancourt |
| 4,292,970 | A | 10/1981 | Hession, Jr. |
| 4,468,224 | A | 8/1984 | Enzmann et al. |
| 4,525,157 | A | 6/1985 | Vaillancourt |
| 4,581,019 | A | 4/1986 | Curelaru et al. |
| 4,594,073 | A | 6/1986 | Stine |
| 4,702,735 | A | 10/1987 | Luther et al. |
| 4,743,265 | A | 5/1988 | Whitehouse et al. |
| 4,766,908 | A | 8/1988 | Clement |
| 4,863,432 | A | 9/1989 | Kvalo |
| 4,950,252 | A | 8/1990 | Luther et al. |
| 4,994,040 | A | 2/1991 | Cameron et al. |
| 5,017,259 | A | 5/1991 | Kohsai |
| 5,040,548 | A | 8/1991 | Yock |
| 5,057,073 | A | 10/1991 | Martin |
| 5,112,312 | A | 5/1992 | Luther |
| 5,115,816 | A | 5/1992 | Lee |
| 5,120,317 | A | 6/1992 | Luther |
| 5,158,544 | A | 10/1992 | Weinstein |
| 5,188,593 | A | 2/1993 | Martin |
| 5,195,962 | A | 3/1993 | Martin et al. |
| 5,207,650 | A | 5/1993 | Martin |
| 5,267,958 | A | 12/1993 | Buchbinder et al. |
| 5,295,970 | A | 3/1994 | Clinton et al. |
| 5,306,247 | A | 4/1994 | Pfenninger |
| 5,322,512 | A | 6/1994 | Mohiuddin |
| 5,328,472 | A | 7/1994 | Steinke et al. |
| 5,350,358 | A | 9/1994 | Martin |
| 5,358,495 | A | 10/1994 | Lynn |
| 5,368,567 | A | 11/1994 | Lee |
| 5,378,230 | A | 1/1995 | Mahurkar |
| 5,380,290 | A | 1/1995 | Makower et al. |
| 5,389,087 | A | 2/1995 | Miraki |
| 5,439,449 | A | 8/1995 | Mapes et al. |
| 5,443,457 | A | 8/1995 | Ginn et al. |
| 5,460,185 | A | 10/1995 | Johnson et al. |
| 5,489,271 | A | 2/1996 | Andersen |
| 5,573,520 | A | 11/1996 | Schwartz et al. |
| 5,683,370 | A | 11/1997 | Luther et al. |
| 5,718,678 | A | 2/1998 | Fleming, III |
| 5,772,636 | A | 6/1998 | Brimhall et al. |
| 5,885,251 | A | 3/1999 | Luther |
| 5,919,164 | A | 7/1999 | Andersen |
| 5,921,971 | A * | 7/1999 | Agro ................ A61M 25/0029 604/523 |
| 5,947,940 | A | 9/1999 | Beisel |
| 5,957,893 | A | 9/1999 | Luther et al. |
| 5,971,957 | A | 10/1999 | Luther et al. |
| 6,159,198 | A | 12/2000 | Gardeski et al. |
| 6,206,849 | B1 | 3/2001 | Martin et al. |
| 6,228,062 | B1 | 5/2001 | Howell et al. |
| 6,475,187 | B1 | 11/2002 | Gerberding |
| 6,606,515 | B1 | 8/2003 | Windheuser et al. |
| 6,626,869 | B1 | 9/2003 | Bint |
| 6,716,228 | B2 | 4/2004 | Tal |
| 6,726,659 | B1 | 4/2004 | Stocking et al. |
| 6,819,951 | B2 | 11/2004 | Patel et al. |
| 6,821,287 | B1 | 11/2004 | Jang |
| 6,926,692 | B2 | 8/2005 | Katoh et al. |
| 6,962,575 | B2 | 11/2005 | Tal |
| 6,991,625 | B1 | 1/2006 | Gately et al. |
| 6,994,693 | B2 | 2/2006 | Tal |
| 6,999,809 | B2 | 2/2006 | Currier et al. |
| 7,025,746 | B2 | 4/2006 | Tal |
| 7,029,467 | B2 | 4/2006 | Currier et al. |
| 7,037,293 | B2 | 5/2006 | Carrillo et al. |
| 7,074,231 | B2 | 7/2006 | Jang |
| 7,141,050 | B2 | 11/2006 | Deal et al. |
| 7,144,386 | B2 | 12/2006 | Korkor et al. |
| 7,311,697 | B2 | 12/2007 | Osborne |
| 7,364,566 | B2 | 4/2008 | Elkins et al. |
| 7,377,910 | B2 | 5/2008 | Katoh et al. |
| 7,390,323 | B2 | 6/2008 | Jang |
| D600,793 | S | 9/2009 | Bierman et al. |
| D601,242 | S | 9/2009 | Bierman et al. |
| D601,243 | S | 9/2009 | Bierman et al. |
| 7,594,911 | B2 | 9/2009 | Powers et al. |
| 7,691,093 | B2 | 4/2010 | Brimhall |
| 7,722,567 | B2 | 5/2010 | Tal |
| D617,893 | S | 6/2010 | Bierman et al. |
| D624,643 | S | 9/2010 | Bierman et al. |
| 7,819,889 | B2 | 10/2010 | Healy et al. |
| 7,857,788 | B2 | 12/2010 | Racz |
| D630,729 | S | 1/2011 | Bierman et al. |
| 7,909,797 | B2 | 3/2011 | Kennedy, II et al. |
| 7,909,811 | B2 | 3/2011 | Agro et al. |
| 7,922,696 | B2 | 4/2011 | Tal et al. |
| 7,938,820 | B2 | 5/2011 | Webster et al. |
| 7,967,834 | B2 | 6/2011 | Tal et al. |
| 7,976,511 | B2 | 7/2011 | Fojtik |
| 7,985,204 | B2 | 7/2011 | Katoh et al. |
| 8,073,517 | B1 | 12/2011 | Burchman |
| 8,105,286 | B2 | 1/2012 | Anderson et al. |
| 8,192,402 | B2 | 6/2012 | Anderson et al. |
| 8,202,251 | B2 | 6/2012 | Bierman et al. |
| 8,206,356 | B2 | 6/2012 | Katoh et al. |
| 8,361,011 | B2 | 1/2013 | Mendels |
| 8,372,107 | B2 | 2/2013 | Tupper |
| 8,377,006 | B2 | 2/2013 | Tal et al. |
| 8,454,577 | B2 | 6/2013 | Joergensen et al. |
| 8,585,858 | B2 | 11/2013 | Kronfeld et al. |
| 8,657,790 | B2 | 2/2014 | Tal et al. |
| 8,672,888 | B2 | 3/2014 | Tal |
| 8,696,645 | B2 | 4/2014 | Tal et al. |
| 8,784,362 | B2 | 7/2014 | Boutilette et al. |
| 8,827,958 | B2 | 9/2014 | Bierman et al. |
| 8,876,704 | B2 | 11/2014 | Golden et al. |
| 8,882,713 | B1 | 11/2014 | Call et al. |
| 8,900,192 | B2 | 12/2014 | Anderson et al. |
| 8,900,207 | B2 | 12/2014 | Uretsky |
| 8,915,884 | B2 | 12/2014 | Tal et al. |
| 8,956,327 | B2 | 2/2015 | Bierman et al. |
| 9,023,093 | B2 | 5/2015 | Pal |
| 9,067,023 | B2 | 6/2015 | Bertocci |
| 9,126,012 | B2 | 9/2015 | McKinnon et al. |
| 9,138,252 | B2 | 9/2015 | Bierman et al. |
| 9,180,275 | B2 | 11/2015 | Helm |
| 9,265,920 | B2 | 2/2016 | Rundquist et al. |
| 9,272,121 | B2 | 3/2016 | Piccagli |
| 9,445,734 | B2 | 9/2016 | Grunwald |
| 9,522,254 | B2 | 12/2016 | Belson |
| 9,554,785 | B2 | 1/2017 | Walters et al. |
| 9,566,087 | B2 | 2/2017 | Bierman et al. |
| 9,675,784 | B2 | 6/2017 | Belson |
| 9,713,695 | B2 | 7/2017 | Bunch et al. |
| 9,764,117 | B2 | 9/2017 | Bierman et al. |
| 9,770,573 | B2 | 9/2017 | Golden et al. |
| 9,814,861 | B2 | 11/2017 | Boutilette et al. |
| 9,820,845 | B2 | 11/2017 | von Lehe et al. |
| 9,861,383 | B2 | 1/2018 | Clark |

(56) References Cited

U.S. PATENT DOCUMENTS

| | | |
|---|---|---|
| 9,872,971 B2 | 1/2018 | Blanchard |
| 9,884,169 B2 | 2/2018 | Bierman et al. |
| 9,889,275 B2 | 2/2018 | Voss et al. |
| 9,913,585 B2 | 3/2018 | McCaffrey et al. |
| 9,913,962 B2 | 3/2018 | Tal et al. |
| 9,981,113 B2 | 5/2018 | Bierman |
| 10,010,312 B2 | 7/2018 | Tegels |
| 10,065,020 B2 | 9/2018 | Gaur |
| 10,086,170 B2 | 10/2018 | Chhikara et al. |
| 10,098,724 B2 | 10/2018 | Adams et al. |
| 10,111,683 B2 | 10/2018 | Tsamir et al. |
| 10,118,020 B2 | 11/2018 | Avneri et al. |
| 10,130,269 B2 | 11/2018 | McCaffrey et al. |
| 10,220,184 B2 | 3/2019 | Clark |
| 10,220,191 B2 | 3/2019 | Belson et al. |
| 10,265,508 B2 | 4/2019 | Baid |
| 10,271,873 B2 | 4/2019 | Steingisser et al. |
| 10,376,675 B2 | 8/2019 | Mitchell et al. |
| 10,675,440 B2 | 6/2020 | Abitabilo et al. |
| 10,806,901 B2 | 10/2020 | Burkholz et al. |
| 10,926,060 B2 | 2/2021 | Stern et al. |
| 11,260,206 B2 | 3/2022 | Stone et al. |
| 2002/0040231 A1 | 4/2002 | Wysoki |
| 2002/0198492 A1 | 12/2002 | Miller et al. |
| 2003/0036712 A1 | 2/2003 | Heh et al. |
| 2003/0060863 A1 | 3/2003 | Dobak |
| 2003/0088212 A1 | 5/2003 | Tal |
| 2003/0100849 A1 | 5/2003 | Jang |
| 2003/0153874 A1 | 8/2003 | Tal |
| 2003/0158514 A1 | 8/2003 | Tal |
| 2004/0015138 A1 | 1/2004 | Currier et al. |
| 2004/0064086 A1 | 4/2004 | Gottlieb et al. |
| 2004/0116864 A1 | 6/2004 | Boudreaux |
| 2004/0116901 A1 | 6/2004 | Appling |
| 2004/0167478 A1 | 8/2004 | Mooney et al. |
| 2004/0193093 A1 | 9/2004 | Desmond |
| 2004/0230178 A1 | 11/2004 | Wu |
| 2005/0004554 A1 | 1/2005 | Osborne |
| 2005/0120523 A1 | 6/2005 | Schweikert |
| 2005/0131343 A1 | 6/2005 | Abrams et al. |
| 2005/0215956 A1 | 9/2005 | Nerney |
| 2005/0245882 A1 | 11/2005 | Elkins et al. |
| 2005/0283221 A1 | 12/2005 | Mann et al. |
| 2006/0009740 A1 | 1/2006 | Higgins et al. |
| 2006/0116629 A1 | 6/2006 | Tal et al. |
| 2006/0129100 A1 | 6/2006 | Tal |
| 2006/0129130 A1 | 6/2006 | Tal et al. |
| 2007/0276288 A1 | 11/2007 | Khaw |
| 2008/0045894 A1 | 2/2008 | Perchik et al. |
| 2008/0125744 A1 | 5/2008 | Treacy |
| 2008/0125748 A1 | 5/2008 | Patel |
| 2008/0132850 A1 | 6/2008 | Fumiyama et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0312578 A1 | 12/2008 | DeFonzo et al. |
| 2008/0319387 A1 | 12/2008 | Amisar et al. |
| 2009/0187147 A1 | 7/2009 | Kurth et al. |
| 2009/0221961 A1 | 9/2009 | Tal et al. |
| 2009/0270889 A1 | 10/2009 | Tal et al. |
| 2010/0030154 A1 | 2/2010 | Duffy |
| 2010/0256487 A1 | 10/2010 | Hawkins et al. |
| 2010/0298839 A1 | 11/2010 | Castro |
| 2010/0305474 A1 | 12/2010 | DeMars et al. |
| 2011/0004162 A1 | 1/2011 | Tal |
| 2011/0009827 A1 | 1/2011 | Bierman et al. |
| 2011/0021994 A1 | 1/2011 | Anderson et al. |
| 2011/0066142 A1 | 3/2011 | Tal et al. |
| 2011/0071502 A1 | 3/2011 | Asai |
| 2011/0144620 A1 | 6/2011 | Tal |
| 2011/0152836 A1 | 6/2011 | Riopelle et al. |
| 2011/0202006 A1 | 8/2011 | Bierman et al. |
| 2011/0251559 A1 | 10/2011 | Tal et al. |
| 2011/0270192 A1 | 11/2011 | Anderson et al. |
| 2012/0041371 A1 | 2/2012 | Tal et al. |
| 2012/0065590 A1 | 3/2012 | Bierman et al. |
| 2012/0078231 A1 | 3/2012 | Hoshinouchi |
| 2012/0130411 A1 | 5/2012 | Tal et al. |
| 2012/0130415 A1 | 5/2012 | Tal et al. |
| 2012/0157854 A1 | 6/2012 | Kurrus et al. |
| 2012/0215171 A1 | 8/2012 | Christiansen |
| 2012/0220942 A1 | 8/2012 | Hall et al. |
| 2012/0226239 A1 | 9/2012 | Green |
| 2012/0283640 A1 | 11/2012 | Anderson et al. |
| 2012/0316500 A1 | 12/2012 | Bierman et al. |
| 2013/0053763 A1 | 2/2013 | Makino et al. |
| 2013/0053826 A1 | 2/2013 | Shevgoor |
| 2013/0123704 A1 | 5/2013 | Bierman et al. |
| 2013/0158338 A1 | 6/2013 | Kelly et al. |
| 2013/0188291 A1 | 7/2013 | Vardiman |
| 2013/0237931 A1 | 9/2013 | Tal et al. |
| 2013/0306079 A1 | 11/2013 | Tracy |
| 2014/0025036 A1 | 1/2014 | Bierman et al. |
| 2014/0081210 A1 | 3/2014 | Bierman et al. |
| 2014/0094774 A1 | 4/2014 | Blanchard |
| 2014/0100552 A1 | 4/2014 | Gallacher et al. |
| 2014/0207052 A1 | 7/2014 | Tal et al. |
| 2014/0207069 A1 | 7/2014 | Bierman et al. |
| 2014/0214005 A1 | 7/2014 | Belson |
| 2014/0257111 A1 | 9/2014 | Yamashita et al. |
| 2014/0276432 A1 | 9/2014 | Bierman et al. |
| 2014/0276599 A1 | 9/2014 | Cully et al. |
| 2015/0080939 A1 | 3/2015 | Adams et al. |
| 2015/0094653 A1 | 4/2015 | Pacheco et al. |
| 2015/0112310 A1 | 4/2015 | Call et al. |
| 2015/0126930 A1 | 5/2015 | Bierman et al. |
| 2015/0148595 A1 | 5/2015 | Bagwell et al. |
| 2015/0190168 A1 | 7/2015 | Bierman et al. |
| 2015/0196210 A1 | 7/2015 | McCaffrey et al. |
| 2015/0224287 A1 | 8/2015 | Bian et al. |
| 2015/0283357 A1 | 10/2015 | Lampropoulos et al. |
| 2015/0297868 A1 | 10/2015 | Tal et al. |
| 2015/0320969 A1 | 11/2015 | Haslinger et al. |
| 2015/0320977 A1 | 11/2015 | Vitullo et al. |
| 2015/0351793 A1 | 12/2015 | Bierman et al. |
| 2015/0359549 A1 | 12/2015 | Lenker et al. |
| 2015/0359998 A1 | 12/2015 | Carmel et al. |
| 2016/0082223 A1 | 3/2016 | Barnell |
| 2016/0114124 A1 | 4/2016 | Tal |
| 2016/0158523 A1 | 6/2016 | Helm |
| 2016/0220786 A1* | 8/2016 | Mitchell ............ A61M 25/0029 |
| 2016/0325073 A1 | 11/2016 | Davies et al. |
| 2016/0338728 A1 | 11/2016 | Tal |
| 2016/0346503 A1 | 12/2016 | Jackson et al. |
| 2017/0035990 A1 | 2/2017 | Swift |
| 2017/0072165 A1 | 3/2017 | Lim et al. |
| 2017/0120000 A1 | 5/2017 | Osypka et al. |
| 2017/0120014 A1 | 5/2017 | Harding et al. |
| 2017/0120034 A1 | 5/2017 | Kaczorowski |
| 2017/0128700 A1 | 5/2017 | Roche Rebollo |
| 2017/0156987 A1 | 6/2017 | Babbs et al. |
| 2017/0172653 A1 | 6/2017 | Urbanski et al. |
| 2017/0239443 A1 | 8/2017 | Abitabilo et al. |
| 2017/0259043 A1 | 9/2017 | Chan et al. |
| 2017/0273713 A1 | 9/2017 | Shah et al. |
| 2017/0326339 A1 | 11/2017 | Bailey et al. |
| 2017/0361070 A1 | 12/2017 | Hivert |
| 2017/0368255 A1 | 12/2017 | Provost et al. |
| 2018/0001062 A1 | 1/2018 | O'Carrol et al. |
| 2018/0021545 A1 | 1/2018 | Mitchell et al. |
| 2018/0116690 A1 | 5/2018 | Sarabia et al. |
| 2018/0117284 A1 | 5/2018 | Appling et al. |
| 2018/0133438 A1 | 5/2018 | Hulvershorn et al. |
| 2018/0154062 A1 | 6/2018 | DeFonzo et al. |
| 2018/0154112 A1 | 6/2018 | Chan et al. |
| 2018/0214674 A1 | 8/2018 | Ebnet et al. |
| 2018/0296799 A1 | 10/2018 | Horst et al. |
| 2018/0296804 A1* | 10/2018 | Bierman ............ A61M 25/0693 |
| 2018/0310955 A1 | 11/2018 | Lindekugel et al. |
| 2019/0015646 A1 | 1/2019 | Matlock et al. |
| 2019/0060616 A1 | 2/2019 | Solomon |
| 2019/0076167 A1 | 3/2019 | Fantuzzi et al. |
| 2019/0134349 A1 | 5/2019 | Cohn et al. |
| 2019/0192824 A1 | 6/2019 | Cordeiro et al. |

(56) References Cited

U.S. PATENT DOCUMENTS

| | | |
|---|---|---|
| 2019/0201665 A1 | 7/2019 | Turpin |
| 2019/0209812 A1 | 7/2019 | Burkholz et al. |
| 2019/0255294 A1 | 8/2019 | Mitchell et al. |
| 2019/0255298 A1 | 8/2019 | Mitchell et al. |
| 2019/0275303 A1 | 9/2019 | Tran et al. |
| 2019/0276268 A1 | 9/2019 | Akingba |
| 2019/0321590 A1 | 10/2019 | Burkholz et al. |
| 2020/0001051 A1 | 1/2020 | Huang et al. |
| 2020/0016374 A1 | 1/2020 | Burkholz et al. |
| 2020/0046948 A1 | 2/2020 | Burkholz et al. |
| 2020/0100716 A1 | 4/2020 | Devgon et al. |
| 2020/0129732 A1 | 4/2020 | Vogt et al. |
| 2020/0147349 A1 | 5/2020 | Holt |
| 2020/0197682 A1 | 6/2020 | Franklin et al. |
| 2020/0197684 A1 | 6/2020 | Wax |
| 2020/0237278 A1 | 7/2020 | Asbaghi |
| 2020/0359995 A1 | 11/2020 | Walsh et al. |
| 2021/0030944 A1 | 2/2021 | Cushen et al. |
| 2021/0069471 A1 | 3/2021 | Howell |
| 2021/0085927 A1 | 3/2021 | Howell |
| 2021/0100985 A1 | 4/2021 | Akcay et al. |
| 2021/0113809 A1 | 4/2021 | Howell |
| 2021/0113810 A1 | 4/2021 | Howell |
| 2021/0113816 A1 | 4/2021 | DiCianni |
| 2021/0121661 A1 | 4/2021 | Howell |
| 2021/0121667 A1 | 4/2021 | Howell |
| 2021/0228842 A1 | 7/2021 | Scherich et al. |
| 2021/0228843 A1 | 7/2021 | Howell et al. |
| 2021/0290898 A1 | 9/2021 | Burkholz |
| 2021/0290901 A1 | 9/2021 | Burkholz et al. |
| 2021/0290913 A1 | 9/2021 | Horst et al. |
| 2021/0322729 A1 | 10/2021 | Howell |
| 2021/0330942 A1 | 10/2021 | Howell |
| 2021/0361915 A1 | 11/2021 | Howell et al. |
| 2021/0402149 A1 | 12/2021 | Howell |
| 2021/0402153 A1 | 12/2021 | Howell et al. |
| 2022/0001138 A1 | 1/2022 | Howell |
| 2022/0032013 A1 | 2/2022 | Howell et al. |
| 2022/0032014 A1 | 2/2022 | Howell et al. |
| 2022/0062528 A1 | 3/2022 | Thornley et al. |
| 2022/0126064 A1 | 4/2022 | Tobin et al. |
| 2022/0193376 A1 | 6/2022 | Spataro et al. |
| 2022/0193377 A1 | 6/2022 | Haymond et al. |
| 2022/0193378 A1 | 6/2022 | Spataro et al. |
| 2022/0323723 A1 | 10/2022 | Spataro et al. |
| 2022/0331563 A1 | 10/2022 | Papadia |
| 2023/0042898 A1 | 2/2023 | Howell et al. |
| 2023/0096377 A1 | 3/2023 | West et al. |
| 2023/0096740 A1 | 3/2023 | Bechstein et al. |
| 2023/0099654 A1 | 3/2023 | Blanchard et al. |
| 2023/0100482 A1 | 3/2023 | Howell |
| 2023/0101455 A1 | 3/2023 | Howell et al. |
| 2023/0102231 A1 | 3/2023 | Bechstein et al. |
| 2023/0233814 A1 | 7/2023 | Howell et al. |

FOREIGN PATENT DOCUMENTS

| | | |
|---|---|---|
| EP | 0730880 A1 | 9/1996 |
| EP | 2061385 A1 | 5/2009 |
| EP | 1458437 B1 | 3/2010 |
| EP | 2248549 A2 | 11/2010 |
| EP | 2319576 A1 | 5/2011 |
| EP | 2366422 A1 | 9/2011 |
| EP | 2486880 A2 | 8/2012 |
| EP | 2486881 A2 | 8/2012 |
| EP | 2486951 A2 | 8/2012 |
| EP | 2512576 A2 | 10/2012 |
| EP | 2152348 B1 | 2/2015 |
| EP | 3473291 A1 | 4/2019 |
| EP | 3093038 B1 | 5/2019 |
| EP | 2260897 B1 | 9/2019 |
| EP | 3693051 A1 | 8/2020 |
| GB | 1273547 A | 5/1972 |
| JP | 2004248987 A | 9/2004 |
| JP | 2008054859 A | 3/2008 |
| WO | 94/21315 A1 | 9/1994 |
| WO | 95/32009 A2 | 11/1995 |
| WO | 98/44979 A1 | 10/1998 |
| WO | 98/53871 A1 | 12/1998 |
| WO | 99/12600 A1 | 3/1999 |
| WO | 99/26681 A1 | 6/1999 |
| WO | 00/06221 A1 | 2/2000 |
| WO | 0054830 A1 | 9/2000 |
| WO | 2003008020 A1 | 1/2003 |
| WO | 2003057272 A2 | 7/2003 |
| WO | 03/068073 A1 | 8/2003 |
| WO | 2003066125 A2 | 8/2003 |
| WO | 2005/096778 A2 | 10/2005 |
| WO | 2006055288 A2 | 5/2006 |
| WO | 2006055780 A2 | 5/2006 |
| WO | 2007046850 A2 | 4/2007 |
| WO | 2008033983 A1 | 3/2008 |
| WO | 2008092029 A2 | 7/2008 |
| WO | 2008/131300 A2 | 10/2008 |
| WO | 2008131289 A2 | 10/2008 |
| WO | 2009114833 A2 | 9/2009 |
| WO | 2009114837 A2 | 9/2009 |
| WO | 2010/048449 A2 | 4/2010 |
| WO | 2010056906 A2 | 5/2010 |
| WO | 2010083467 A2 | 7/2010 |
| WO | 2010/132608 A2 | 11/2010 |
| WO | 2011081859 A2 | 7/2011 |
| WO | 2011097639 A2 | 8/2011 |
| WO | 2011/109792 A1 | 9/2011 |
| WO | 2011146764 A1 | 11/2011 |
| WO | 2012068162 A2 | 5/2012 |
| WO | 2012068166 A2 | 5/2012 |
| WO | 2012135761 A1 | 10/2012 |
| WO | 2012/154277 A1 | 11/2012 |
| WO | 2012162677 A1 | 11/2012 |
| WO | 2013026045 A1 | 2/2013 |
| WO | 2013138519 A1 | 9/2013 |
| WO | 2014006403 A1 | 1/2014 |
| WO | 2014/100392 A1 | 6/2014 |
| WO | 2014113257 A2 | 7/2014 |
| WO | 2014152005 A2 | 9/2014 |
| WO | 2014197614 A2 | 12/2014 |
| WO | 2015057766 A1 | 4/2015 |
| WO | 2015077560 A1 | 5/2015 |
| WO | 2015/168655 A2 | 11/2015 |
| WO | 2016110824 A1 | 7/2016 |
| WO | 2016123278 A1 | 8/2016 |
| WO | 2016139590 A1 | 9/2016 |
| WO | 2016139597 A2 | 9/2016 |
| WO | 2016/178974 A1 | 11/2016 |
| WO | 2016/187063 A1 | 11/2016 |
| WO | 2016176065 A1 | 11/2016 |
| WO | 2018089275 A1 | 5/2018 |
| WO | 2018089285 A1 | 5/2018 |
| WO | 2018089385 A1 | 5/2018 |
| WO | 2018191547 A1 | 10/2018 |
| WO | 2018213148 A1 | 11/2018 |
| WO | 2018218236 A1 | 11/2018 |
| WO | 2019/050576 A1 | 3/2019 |
| WO | 2019/146026 A1 | 8/2019 |
| WO | 2019199734 A1 | 10/2019 |
| WO | 2020014149 A1 | 1/2020 |
| WO | 2020069395 A1 | 4/2020 |
| WO | 2020/109448 A1 | 6/2020 |
| WO | 2020/113123 A1 | 6/2020 |
| WO | 2021050302 A1 | 3/2021 |
| WO | 2021/077103 A1 | 4/2021 |
| WO | 2021062023 A1 | 4/2021 |
| WO | 2021081205 A1 | 4/2021 |
| WO | 2021086793 A1 | 5/2021 |
| WO | 2021/236950 A1 | 11/2021 |
| WO | 2022/031618 A1 | 2/2022 |
| WO | 2022/094141 A1 | 5/2022 |
| WO | 2022/133297 A1 | 6/2022 |
| WO | 2022-140406 A1 | 6/2022 |
| WO | 2022/140429 A1 | 6/2022 |
| WO | 2022/217098 A1 | 10/2022 |
| WO | 2023014994 A1 | 2/2023 |
| WO | 2023049498 A1 | 3/2023 |

(56) References Cited

FOREIGN PATENT DOCUMENTS

| | | | |
|---|---|---|---|
| WO | 2023049505 | A1 | 3/2023 |
| WO | 2023049511 | A1 | 3/2023 |
| WO | 2023049519 | A1 | 3/2023 |
| WO | 2023049522 | A1 | 3/2023 |

OTHER PUBLICATIONS

PCT/US2020/052536 filed Sep. 24, 2020 International Search Report and Written Opinion dated Dec. 4, 2020.
PCT/US2020/056364 filed Oct. 19, 2020 International Search Report and Written Opinion dated Jan. 19, 2021.
PCT/US2020/056864 filed Oct. 22, 2020 International Search Report and Written Opinion dated Jan. 14, 2021.
PCT/US2020/057202 filed Oct. 23, 2020 International Search Report and Written Opinion dated Jan. 21, 2021.
PCT/US2020/057397 filed Oct. 26, 2020 International Search Report and Written Opinion dated Mar. 10, 2021.
U.S. Appl. No. 15/008,628, filed Jan. 28, 2016 Final Office Action dated May 30, 2018.
U.S. Appl. No. 15/008,628, filed Jan. 28, 2016 Non-Final Office Action dated Jan. 25, 2019.
U.S. Appl. No. 15/008,628, filed Jan. 28, 2016 Non-Final Office Action dated Nov. 2, 2017.
U.S. Appl. No. 15/008,628, filed Jan. 28, 2016 Notice of Allowance dated May 15, 2019.
U.S. Appl. No. 16/398,020, filed Apr. 29, 2019 Non-Final Office Action dated May 11, 2021.
PCT/US2022/039614 filed Aug. 5, 2022 International Search Report and Written Opinion dated Dec. 22, 2022.
PCT/US2022/044848 filed Sep. 27, 2022 International Search Report and Written Opinion dated Feb. 3, 2023.
PCT/US2022/044879 filed Sep. 27, 2022 International Search Report and Written Opinion dated Mar. 3, 2023.
PCT/US2022/044901 filed Sep. 27, 2022 International Search Report and Written Opinion dated Mar. 3, 2023.
PCT/US2022/044918 filed Sep. 27, 2022 International Search Report and Written Opinion dated Feb. 21, 2023.
PCT/US2022/044923 filed Sep. 27, 2022 International Search Report and Written Opinion dated Feb. 15, 2023.
U.S. Appl. No. 17/326,017, filed May 20, 2021 Non-Final Office Action dated Jan. 26, 2023.
U.S. Appl. No. 17/390,682, filed Jul. 30, 2021 Non-Final Office Action dated Mar. 2, 2023.
U.S. Appl. No. 17/392,061, filed Aug. 2, 2021 Restriction Requirement dated Mar. 30, 2023.
PCT/US2021/039084 filed Jun. 25, 2021 International Search Report and Written Opinion dated Jan. 10, 2022.
PCT/US2021/039843 filed Jun. 30, 2021 International Search Report and Written Opinion dated Nov. 11, 2021.
U.S. Appl. No. 16/398,020, filed Apr. 29, 2019 Final Office Action dated Jan. 25, 2022.
U.S. Appl. No. 17/006,553, filed Aug. 28, 2020 Non-Final Office Action dated Mar. 16, 2022.
U.S. Appl. No. 17/077,728, filed Oct. 22, 2020 Non-Final Office Action dated Feb. 9, 2022.
PCT/US2021/028018 filed Apr. 19, 2021 International Preliminary Report on Patentability dated Jun. 3, 2022.
PCT/US2021/064174 filed Dec. 17, 2021 International Search Report and Written Opinion dated May 18, 2022.
PCT/US2021/064671 filed Dec. 21, 2021 International Search Report and Written Opinion dated May 27, 2022.
PCT/US2022/024085 filed Apr. 8, 2022 International Search Report and Wirtten Opinion dated Sep. 12, 2022.
U.S. Appl. No. 16/398,020, filed Apr. 29, 2019 Examiner's Answer dated Oct. 31, 2022.
U.S. Appl. No. 17/031,478, filed Sep. 24, 2020 Notice of Allowance dated Sep. 16, 2022.
U.S. Appl. No. 17/156,252, filed Jan. 22, 2021 Non-Final Office Action dated Oct. 25, 2022.
PCT/US2021/028683 filed Apr. 22, 2021 International Search Report and Written Opinion dated Sep. 16, 2021.
PCT/US2021/029183 filed Apr. 26, 2021 International Search Report and Written Opinion dated Sep. 24, 2021.
PCT/US2021/033443 filed May 20, 2021 International Search Report and Written Opinion dated Sep. 23, 2021.
PCT/US2021/044029 filed Jul. 30, 2021 International Search Report and Written Opinion dated Dec. 9, 2021.
PCT/US2021/057135 filed Oct. 28, 2021 International Preliminary Report on Patentability dated May 2, 2023.
PCT/US2021/057135 filed Oct. 28, 2021 International Search Report and Written Opinion dated Mar. 11, 2022.
PCT/US2023/011173 filed Jan. 19, 2023 International Search Report and Written Opinion dated May 22, 2023.
U.S. Appl. No. 17/156,252, filed Jan. 22, 2021 Notice of Allowance dated Apr. 24, 2023.
U.S. Appl. No. 17/240,591, filed Apr. 26, 2021 Non-Final Office Action dated Jun. 8, 2023.
U.S. Appl. No. 17/358,504, filed Jun. 25, 2021 Restriction Requirement dated Jun. 7, 2023.
PCT/US2021/044223 filed Aug. 2, 2021 International Search Report and Written Opinion dated Dec. 21, 2021.
PCT/US2021/048275 filed Aug. 30, 2021 International Search Report and Written Opinion dated Jan. 4, 2022.
PCT/US2021/064642 filed Dec. 21, 2021 International Search Report and Written Opinion dated May 11, 2022.
U.S. Appl. No. 17/031,478, filed Sep. 24, 2020 Non-Final Office Action dated May 11, 2022.
U.S. Appl. No. 17/156,252, filed Jan. 22, 2021 Notice of Allowance dated Aug. 9, 2023.
U.S. Appl. No. 17/326,017, filed May 20, 2021 Notice of Allowance dated Jul. 3, 2023.
U.S. Appl. No. 17/358,504, filed Jun. 25, 2021 Non-Final Office Action dated Oct. 4, 2023.
U.S. Appl. No. 17/360,694, filed Jun. 28, 2021 Restriction Requirement dated Jul. 20, 2023.
U.S. Appl. No. 17/390,682, filed Jul. 30, 2021 Final Office Action dated Jul. 27, 2023.
U.S. Appl. No. 17/392,061, filed Aug. 2, 2021 Non-Final Office Action dated Jul. 17, 2023.
U.S. Appl. No. 17/513,789, filed Oct. 28, 2021 Restriction Requirement dated Oct. 3, 2023.
PCT/US2021/014700 filed Jan. 22, 2021 International Search Report and Written Opinion dated Jun. 29, 2021.
PCT/US2021/028018 filed Apr. 19, 2021 International Search Report and Written Opinion dated Sep. 13, 2021.
U.S. Appl. No. 16/398,020, filed Apr. 29, 2019 Board Decision dated Oct. 30, 2023.
U.S. Appl. No. 17/240,591, filed Apr. 26, 2021 Final Office Action dated Dec. 6, 2023.
U.S. Appl. No. 17/360,694, filed Jun. 28, 2021 Non-Final Office Action dated Oct. 13, 2023.
U.S. Appl. No. 17/390,682, filed Jul. 30, 2021 Non-Final Office Action dated Dec. 1, 2023.
U.S. Appl. No. 17/392,061, filed Aug. 2, 2021 Final Office Action dated Nov. 21, 2023.
U.S. Appl. No. 17/557,924, filed Dec. 21, 2021 Non-Final Office Action dated Nov. 3, 2023.

\* cited by examiner

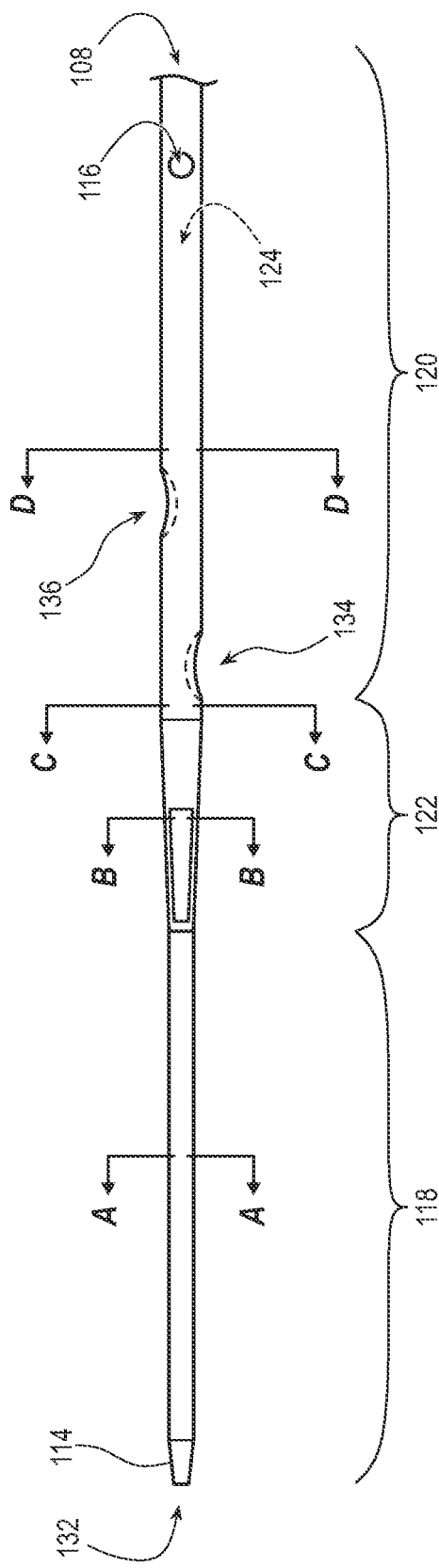
FIG. 9
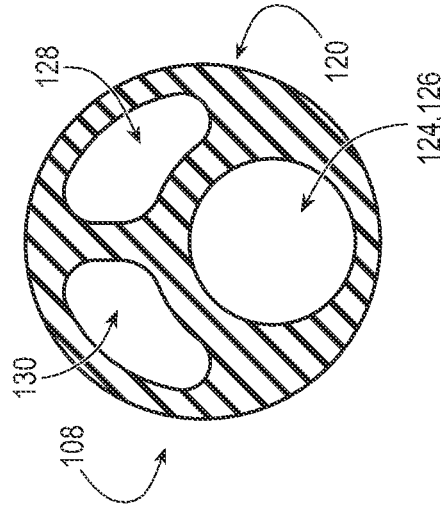
FIG. 12
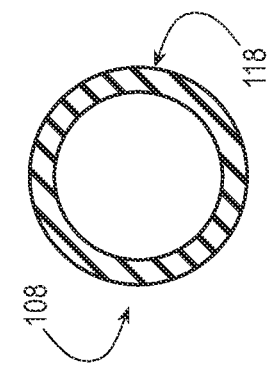
FIG. 11
FIG. 10

RAPIDLY INSERTABLE CENTRAL CATHETERS INCLUDING CATHETER ASSEMBLIES AND METHODS THEREOF

PRIORITY

This application claims the benefit of priority to U.S. Patent Application Ser. No. 63/014,555, filed Apr. 23, 2020, which is incorporated by reference in its entirety into this application.

BACKGROUND

A central venous catheter ("CVC") is formed of a material having a relatively low durometer, which contributes to the CVC having a lack of column strength. Due to the lack of column strength, CVCs are commonly introduced into patients and advanced through their vasculatures by way of the Seldinger technique. The Seldinger technique utilizes a number of steps and medical devices (e.g., a needle, a scalpel, a guidewire, an introducer sheath, a dilator, a CVC, etc.). While the Seldinger technique is effective, the number of steps is time consuming, handling the number of medical devices is awkward, and both of the foregoing can lead to patient trauma. In addition, there is a relatively high potential for touch contamination due to the number of medical devices that need to be interchanged during the number of steps of the Seldinger technique. As such, there is a need to reduce the number of steps and medical devices involved in introducing a catheter such as a CVC into a patient and advancing the catheter through a vasculature thereof.

Disclosed herein are rapidly insertable central catheters ("RICCs") including catheter assemblies and methods thereof that address the foregoing.

SUMMARY

Disclosed herein is a RICC assembly. The RICC assembly includes, in some embodiments, a RICC, an introducer, and a coupling system configured to couple the RICC and the introducer together. The RICC includes a catheter tube, a catheter hub, and one or more extension legs. The catheter tube includes a first section formed of a first material having a first durometer and a second section formed of a second material having a second durometer less than the first durometer. The catheter tube includes a side aperture through a side of the catheter tube in a distal-end portion thereof but proximal of the first section of the catheter tube. The side aperture opens into an introducing lumen of the catheter tube that extends from at least the side aperture to a distal end of the RICC. The catheter hub is coupled to a proximal-end portion of the catheter tube. Each extension leg of the one-or-more extension legs is coupled to the catheter hub by a distal-end portion thereof. The introducer includes an introducer needle having a cannula extending through the distal end of the RICC when the RICC assembly is in at least a ready-to-deploy state of the RICC assembly. The coupling system includes a distal coupler slidably attached to the catheter tube proximal of the side aperture.

In some embodiments, the cannula further extends through a longitudinal through hole of the distal coupler, through the side aperture of the catheter tube, and along the introducing lumen of the catheter tube before exiting through the distal end of the RICC when the RICC assembly is in at least the ready-to-deploy state thereof In some embodiments, the distal coupler includes a tab configured to allow a clinician to single handedly advance the RICC off the cannula with a single finger of a hand while holding the introducer between a thumb and another finger or fingers of the hand.

In some embodiments, the introducer further includes a syringe and an access guidewire. The syringe has a syringe tip coupled to a needle hub of the introducer needle. The access guidewire is disposed in an access-guidewire lumen formed of at least a plunger lumen of a plunger of the syringe and a needle lumen of the introducer needle. The access guidewire has a length sufficient for extension of the access guidewire through the distal end of the RICC.

In some embodiments, the plunger includes a sealing mechanism in a proximal-end portion of the plunger for sealing off the access-guidewire lumen. The sealing mechanism is configured to prevent blood from discharging through a proximal end of the plunger during a venipuncture or while withdrawing the access guidewire from a blood-vessel lumen of a patient.

In some embodiments, the access guidewire is captively disposed in the introducer by a stop about a proximal-end portion of the access guidewire and a closed end of an access-guidewire sterile barrier of a fixed length coupled to the proximal end of the plunger. The stop provides a distal limit to advancing the access guidewire. The closed end of the access-guidewire sterile barrier around the access guidewire provides a proximal limit to withdrawing the access guidewire.

In some embodiments, the introducer further includes a fluid-pressure indicator extending from a side arm of the needle hub. The fluid-pressure indicator is fluidly coupled to the needle lumen of the introducer needle by way of a side-arm lumen of the side arm for observing blood flashback.

In some embodiments, the coupling system further includes a proximal coupler slidably attached to the catheter hub and removably attached to the syringe in at least the ready-to-deploy state of the RICC assembly. The coupling system is configured to allow the RICC to slide relative to the introducer.

In some embodiments, the proximal coupler includes a catheter-hub clip from which the RICC is configured to suspend by the catheter hub in at least the ready-to-deploy state of the RICC assembly. The RICC is configured to suspend from the catheter-hub clip by the one-or-more extension legs when the proximal coupler is advanced thereover in an operating state of the RICC assembly.

In some embodiments, the proximal coupler includes a syringe clip. The introducer is configured to rest in the syringe clip by a distal-end portion of a barrel of the syringe in at least the ready-to-deploy state of the RICC assembly.

In some embodiments, the RICC further includes a collapsible catheter-tube sterile barrier over the catheter tube between the catheter hub and the distal coupler to which distal coupler the catheter-tube sterile barrier is coupled. The catheter-tube sterile barrier is configured to split apart when a sterile-barrier tab of the catheter-tube sterile barrier is removed from the catheter-hub clip and the catheter-tube sterile barrier is pulled away from the catheter tube by the sterile-barrier tab.

In some embodiments, the catheter-tube sterile barrier has sufficient tensile strength to pull the distal coupler off the catheter tube without breaking when the catheter-tube sterile barrier splits down to the distal coupler while being pulled away from the catheter tube.

In some embodiments, the RICC includes a set of three lumens including a distal lumen, a medial lumen, and a proximal lumen. The set of three lumens is formed of fluidly connected portions of three catheter-tube lumens, three hub lumens, and three extension-leg lumens. The introducing lumen of the catheter tube is coincident with a distal-end portion of the distal lumen.

In some embodiments, the distal lumen has a distal-lumen aperture in a distal end of the RICC, the medial lumen has a medial-lumen aperture in the side of the catheter tube distal of the side aperture, and the proximal lumen has a proximal-lumen aperture in the side of the catheter tube distal of the side aperture but proximal of the medial-lumen aperture.

In some embodiments, the RICC further includes a maneuver guidewire disposed in the distal lumen. The maneuver guidewire has a length sufficient for extension of the maneuver guidewire to a lower ⅓ of a superior vena cava of a heart. The maneuver guidewire is captively disposed in the RICC by a stop about a proximal-end portion of the maneuver guidewire and a closed end of a maneuver-guidewire sterile barrier of a fixed length coupled to a Luer connector. The stop provides a distal limit to advancing the maneuver guidewire. The closed end of the maneuver-guidewire sterile barrier around the maneuver guidewire provides a proximal limit to withdrawing the maneuver guidewire.

Also disclosed herein is a method for inserting a RICC into a blood-vessel lumen of a patient. The method includes, in some embodiments, a RICC assembly-obtaining step, a needle tract-establishing step, a first RICC-advancing step, and an introducer-withdrawing step. The RICC assembly-obtaining step includes obtaining a RICC assembly. The RICC assembly includes the RICC, an introducer, and a coupling system that couples the RICC and the introducer together. The introducer includes a syringe coupled to an introducer needle. The coupling system includes a distal coupler that couples the RICC and the introducer together by distal-end portions thereof in at least a ready-to-deploy state of the RICC assembly. The needle tract-establishing step includes establishing a needle tract from an area of skin to the blood-vessel lumen of the patient with a cannula of the introducer needle while holding a distal-end portion of a barrel of the syringe. The cannula extends through a longitudinal through hole of the distal coupler, through a side aperture in a distal-end portion of a catheter tube of the RICC, along an introducing lumen of the catheter tube, and out a distal end of the RICC for establishing the needle tract. The first RICC-advancing step includes advancing a distal-end portion of the catheter tube into the blood-vessel lumen over the cannula. The introducer-withdrawing step includes withdrawing the cannula from the introducing lumen by way of the side aperture of the catheter tube.

In some embodiments, the method further includes a blood-aspirating step. The blood-aspirating step includes aspirating blood with the syringe before withdrawing the cannula from the introducing lumen. The blood-aspirating step confirms the cannula is disposed in the blood-vessel lumen of the patient.

In some embodiments, the needle tract-establishing step includes ensuring blood flashes back into a needle hub of the introducer needle, a side arm of the needle hub, or a fluid-pressure indicator extending from the side arm of the needle hub.

In some embodiments, the needle tract-establishing step includes holding the barrel by a syringe clip around the distal-end portion of the barrel. The syringe clip is part of a proximal coupler of the coupling system.

In some embodiments, the first RICC-advancing step includes advancing the catheter tube into the blood-vessel lumen with a single finger of a hand while holding the barrel of the syringe by the syringe clip between a thumb and another finger or fingers of the hand. The distal coupler includes a tab configured for advancing the catheter tube into the blood-vessel lumen with the single finger.

In some embodiments, the first RICC-advancing step includes advancing a catheter hub of the RICC from a catheter-hub clip of the proximal coupler. After advancing the catheter hub from the catheter-hub clip, one or more extension legs of the RICC are advanced within the catheter-hub clip. The RICC is configured to suspend from the coupling system until at least withdrawing the cannula from both the introducing lumen and the longitudinal through hole of the distal coupler.

In some embodiments, the method further includes an access guidewire-advancing step. The access guidewire-advancing step includes advancing an access guidewire disposed in an access-guidewire lumen formed of at least a plunger lumen of a plunger of the syringe and a needle lumen of the introducer needle into the blood-vessel lumen beyond a distal end of the cannula before the first RICC-advancing step.

In some embodiments, the method further includes a maneuver guidewire-advancing step. The maneuver guidewire-advancing step includes advancing a maneuver guidewire into the blood-vessel lumen by way of a distal lumen having a distal-lumen aperture in the distal end of the RICC. The introducing lumen of the catheter tube is coincident with a distal-end portion of the distal lumen, thereby mandating withdrawing the cannula from the introducing lumen before the maneuver guidewire-advancing step.

In some embodiments, the method further includes a second RICC-advancing step. The second RICC-advancing step includes advancing the distal-end portion of the catheter tube farther into the blood-vessel lumen over the maneuver guidewire. The second RICC-advancing step includes concomitantly sliding the distal coupler proximally toward a proximal-end portion of the catheter tube to uncover the catheter tube. The catheter tube is covered by a collapsible sterile barrier between the proximal-end portion of the catheter tube and the distal coupler in at least the ready-to-deploy state of the RICC assembly.

In some embodiments, the method further includes a sterile barrier-removing step. The sterile barrier-removing step includes removing the sterile barrier and the distal coupler from the RICC by pulling a sterile-barrier tab of the sterile barrier opposite the distal coupler away from the catheter tube to split the sterile barrier apart, then pulling the distal coupler from the catheter tube by the sterile barrier to which the distal coupler is slidably attached.

In some embodiments, the catheter tube includes a first section formed of a first material having a first durometer and a second section proximal of the first section formed of a second material having a second durometer less than the first durometer. The first section of the catheter tube is configured with a column strength for advancing the catheter tube into the blood-vessel lumen over the access guidewire or the maneuver guidewire.

These and other features of the concepts provided herein will become more apparent to those of skill in the art in view of the accompanying drawings and following description, which describe particular embodiments of such concepts in greater detail.

DRAWINGS

FIG. 9 illustrates a distal-end portion of a catheter tube of the RICC in accordance with some embodiments.

FIG. 10 illustrates a first transverse cross section of the catheter tube in accordance with some embodiments.

FIG. 11 illustrates a second transverse cross section of the catheter tube in accordance with some embodiments.

FIG. 12 illustrates a third or fourth transverse cross section of the catheter tube in accordance with some embodiments.

DESCRIPTION

Figure 1:
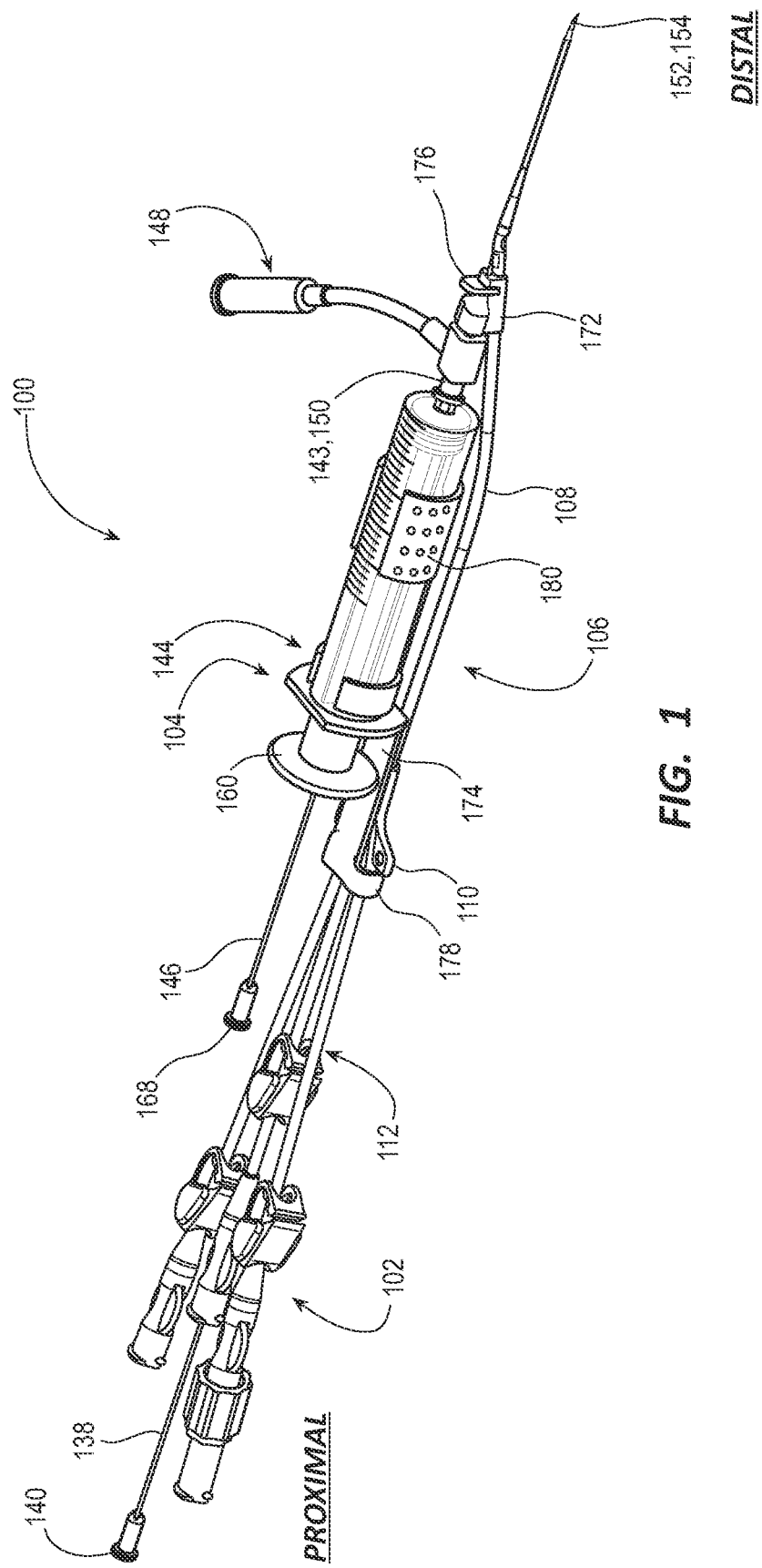
FIG. 1 illustrates an oblique view of a RICC assembly including a RICC, an introducer, and a coupling system in accordance with some embodiments.
Figure 2:
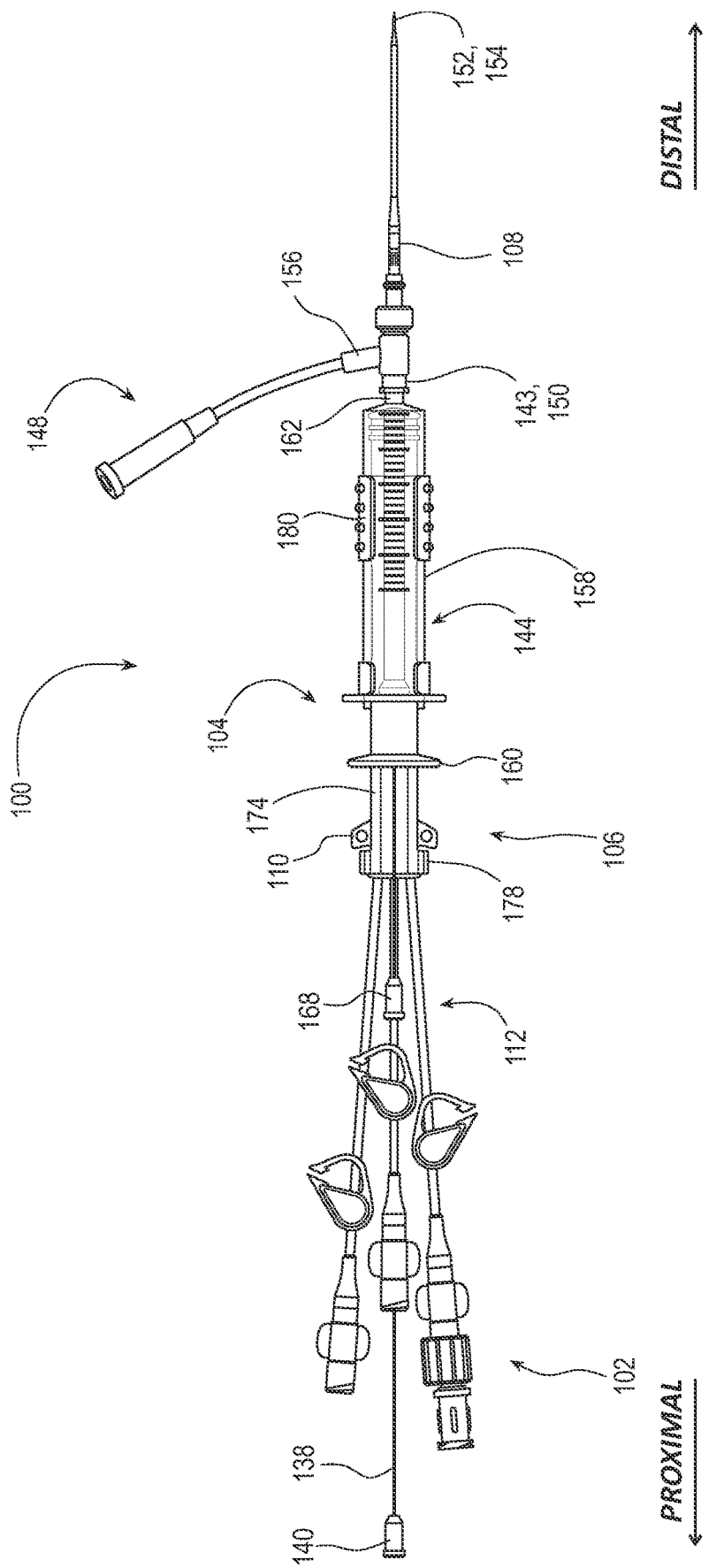
FIG. 2 illustrates a top view of the RICC assembly in accordance with some embodiments.
Figure 3:
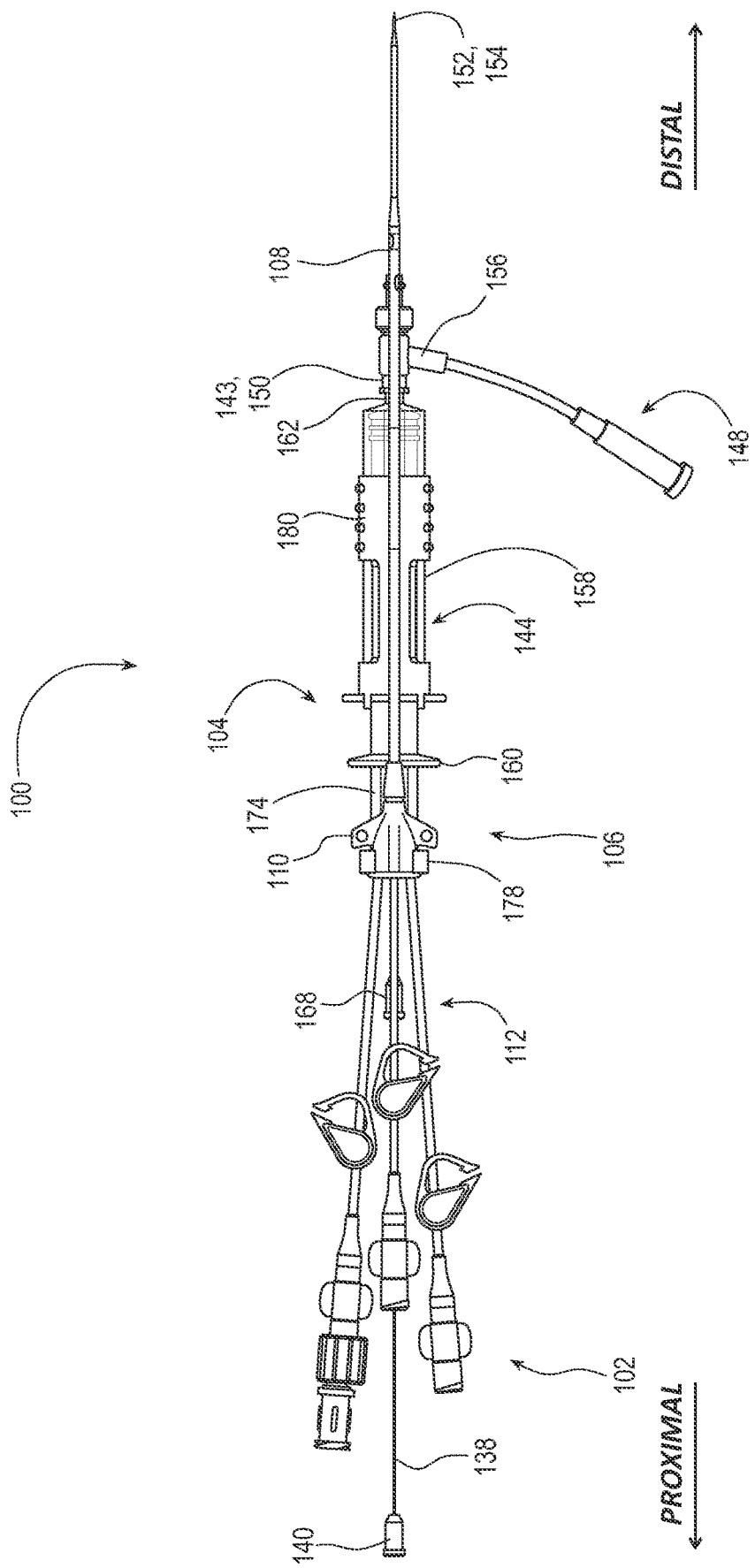
FIG. 3 illustrates a bottom view of the RICC assembly in accordance with some embodiments.
Figure 4:
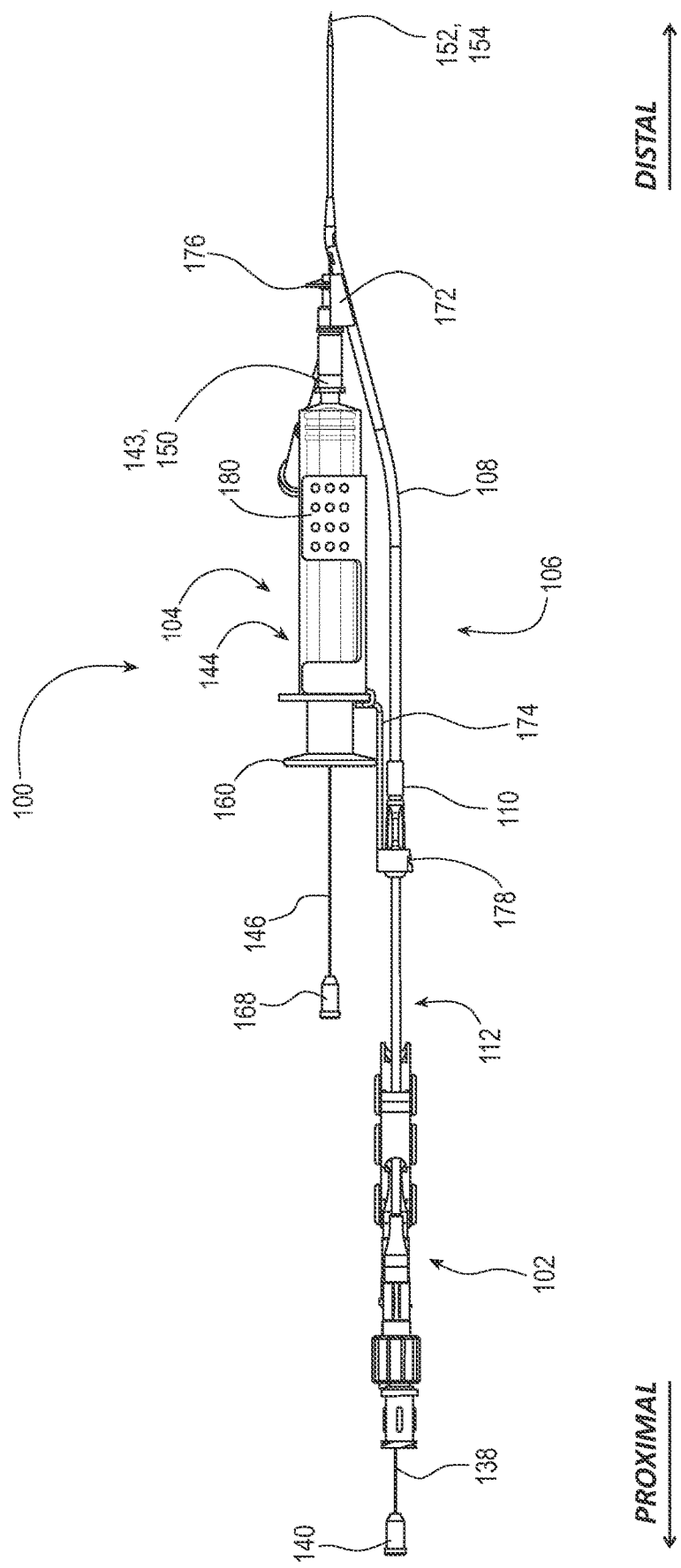
FIG. 4 illustrates a side view of the RICC assembly in accordance with some embodiments.
Figure 5:
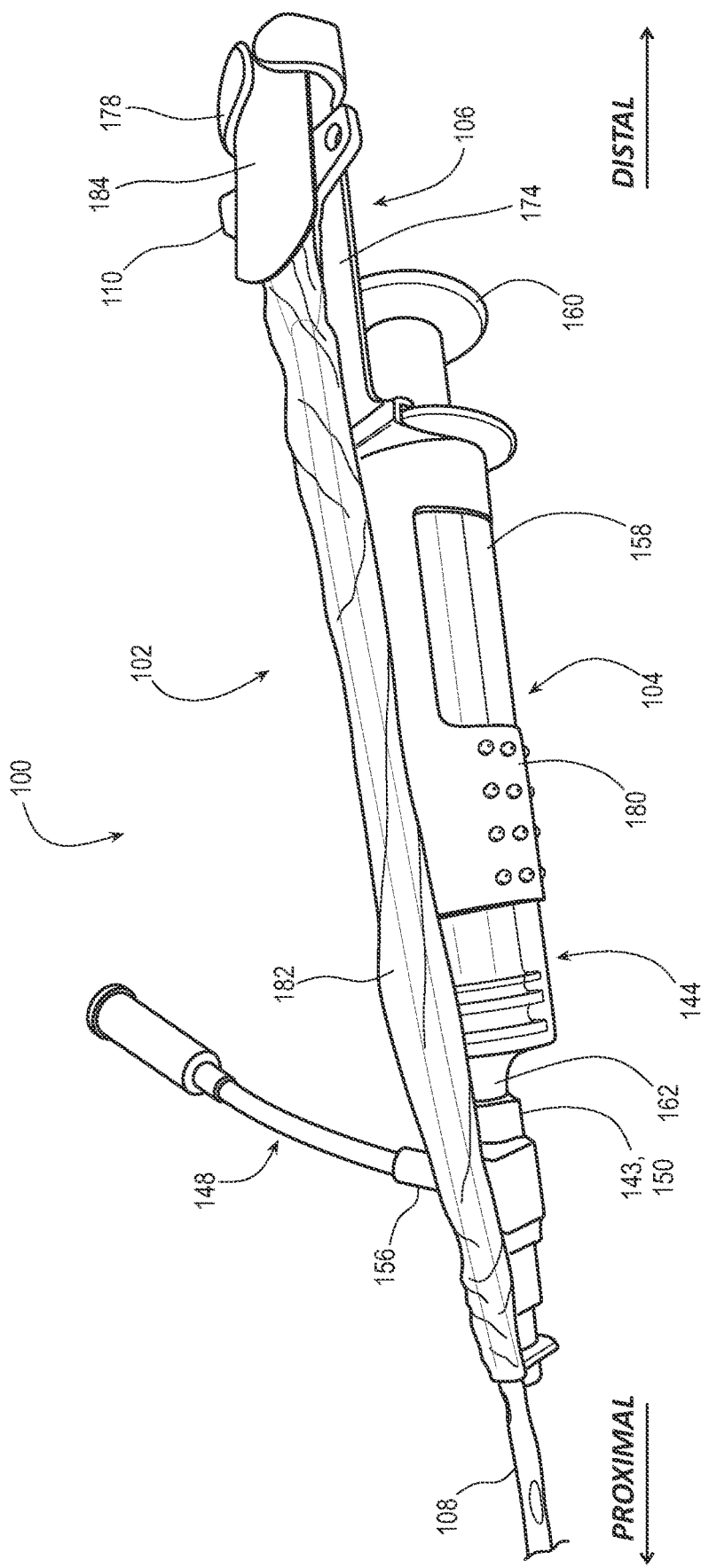
FIG. 5 illustrates a detailed view of a bottom of the RICC assembly in accordance with some embodiments.
Figure 6:
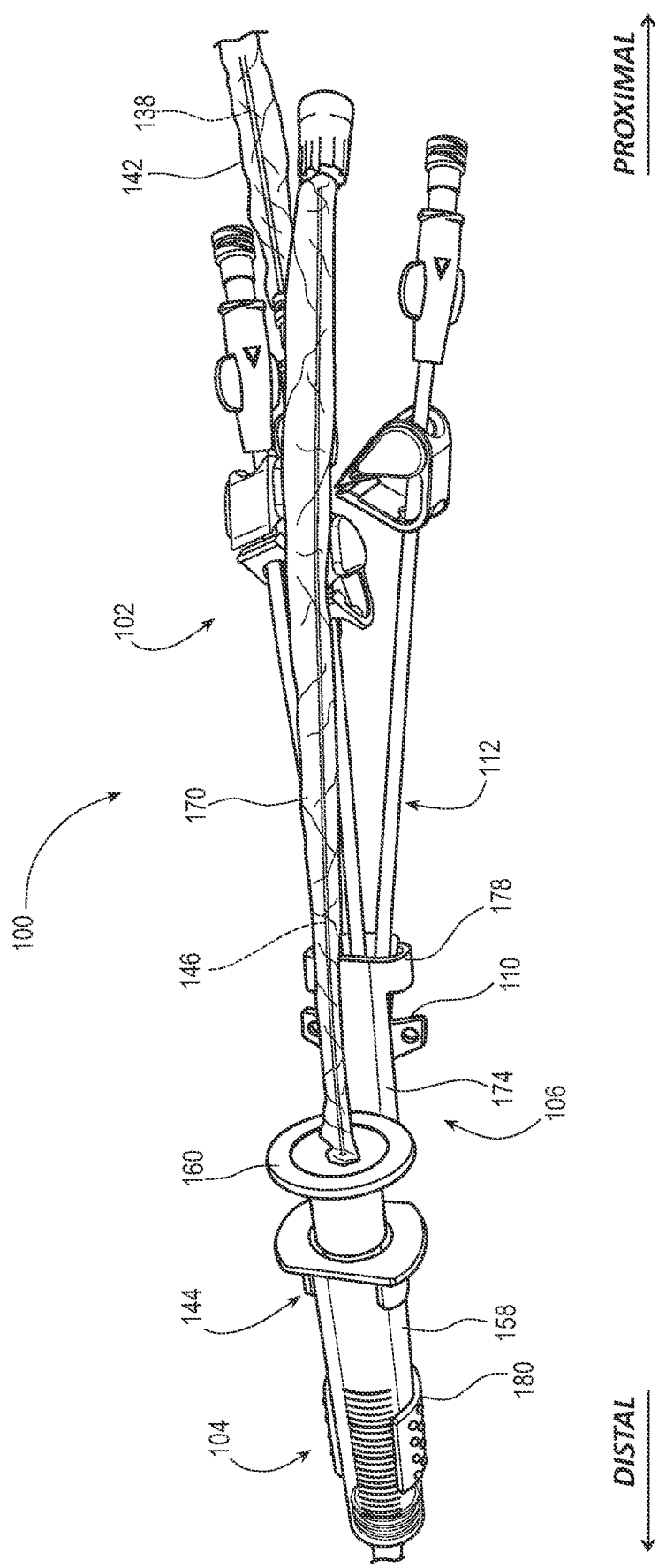
FIG. 6 illustrates a detailed view of a top of the RICC assembly in accordance with some embodiments.
Figure 7:
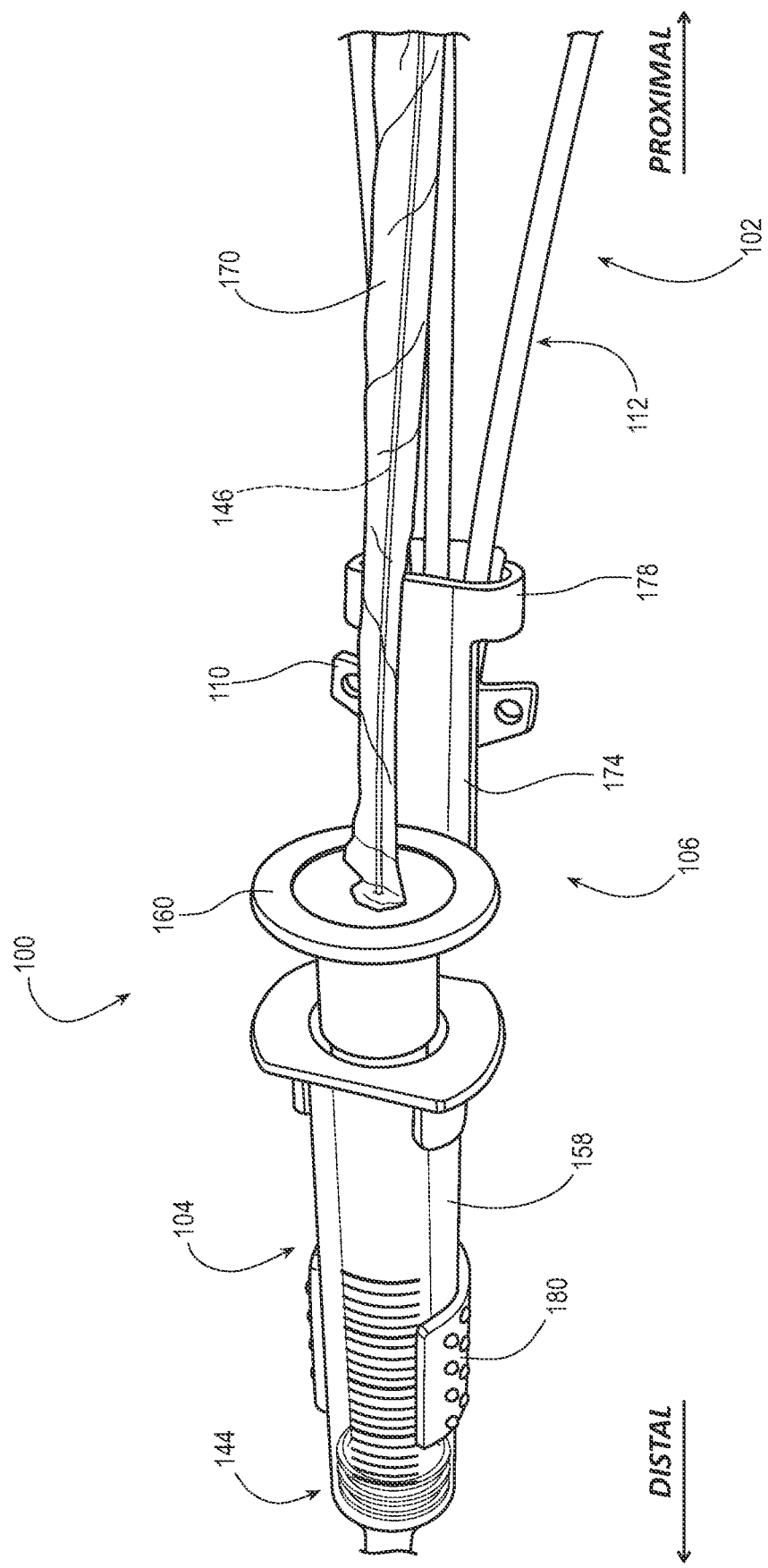
FIG. 7 illustrates another detailed view of the top of the RICC assembly in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, there is a need to reduce the number of steps and medical devices involved in introducing a catheter such as a CVC into a patient and advancing the catheter through a vasculature thereof.

Disclosed herein are rapidly insertable central catheters ("RICCs") including catheter assemblies and methods thereof that address the foregoing. However, it should be understood the RICCs are but one type of catheter in which the concepts provided herein can be embodied or otherwise incorporated. Indeed, peripherally inserted central catheters ("PICCs"), dialysis catheters, or the like can also embody or otherwise incorporate the concepts provided herein for the RICCs, as well as catheter assemblies and methods thereof.

RICC Assemblies

Figure 8:
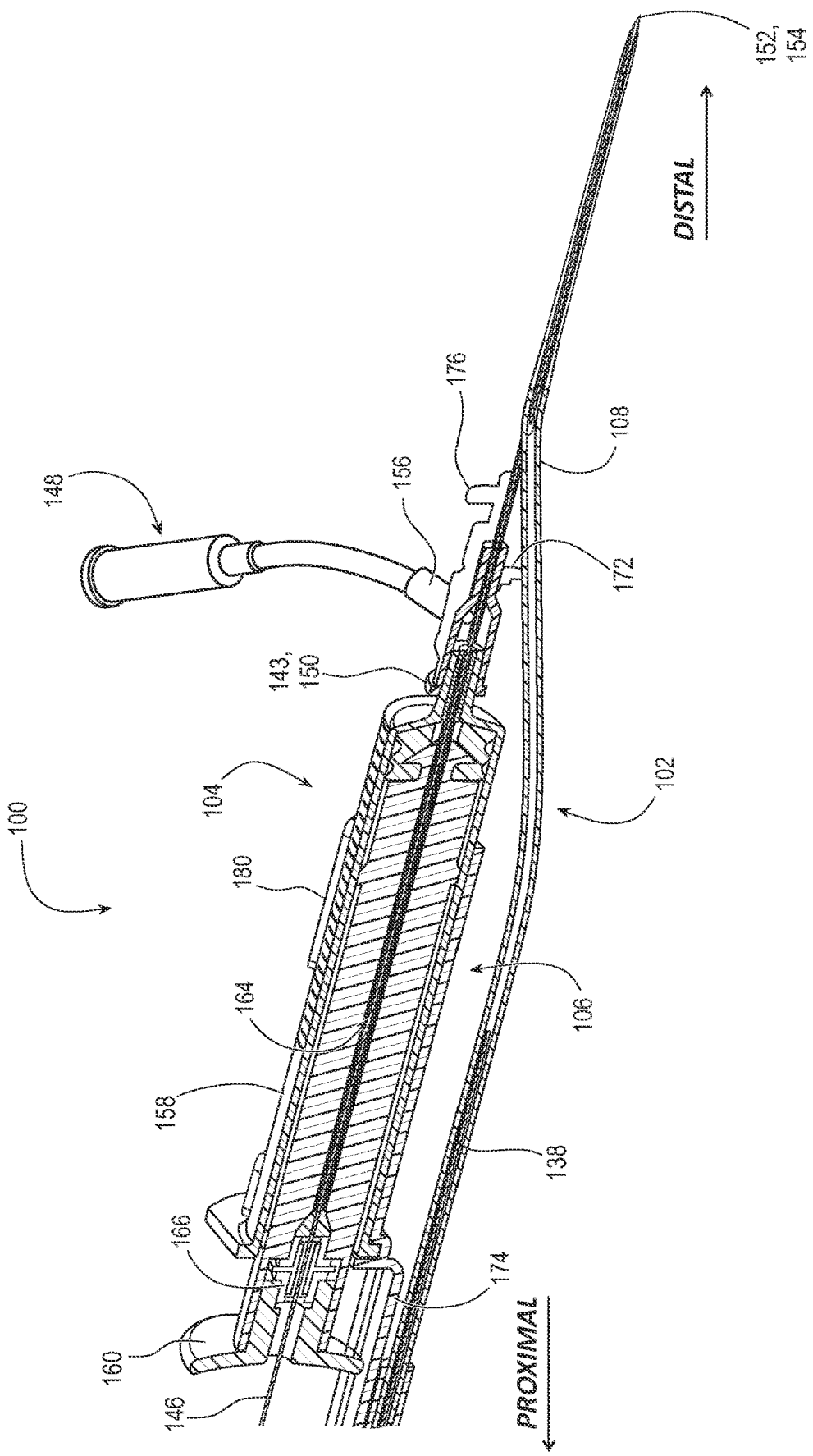
FIG. 8 illustrates a longitudinal cross section of the RICC assembly in accordance with some embodiments.

FIGS. 1-7 illustrate various views of a RICC assembly 100 including a RICC 102, an introducer 104, and a coupling system 106 in accordance with some embodiments. FIG. 8 illustrates a longitudinal cross section of the RICC assembly 100 in accordance with some embodiments. FIG. 9 illustrates a distal-end portion of a catheter tube 108 of the RICC 102 in accordance with some embodiments. FIGS. 10-12 illustrate various transverse cross-sections of the catheter tube 108 in accordance with some embodiments.

As shown, the RICC assembly 100 includes, in some embodiments, the RICC 102, the introducer 104, and the coupling system 106 configured to couple the RICC 102 and the introducer 104 together. The RICC 102, the introducer 104, and the coupling system 106 are described, in turn, in sections set forth below; however, some crossover between the sections for the RICC 102, the introducer 104, and the coupling system 106 exist in view of the interrelatedness of the RICC 102, the introducer 104, and the coupling system 106 in the RICC assembly 100.

The RICC 102 includes the catheter tube 108, a catheter hub 110, and one or more extension legs 112.

The catheter tube 108 includes two or more sections including a tip 114 in a distal-end portion of the catheter tube 108, one or more catheter-tube lumens, and a side aperture 116 through a side of the catheter tube 108 in the distal-end portion of the catheter tube 108.

The two or more sections of the catheter tube 108 can be a main body of the catheter tube 108 and the tip 114, which can be formed as a single extruded piece of a single material or a single coextruded piece of two similar materials.

Alternatively, the main body of the catheter tube 108 and the tip 114 can be formed as two different extruded pieces of two similar materials and subsequently coupled. However, FIG. 9 illustrates an embodiment of the catheter tube 108 in which the catheter tube 108 is formed as two different extruded pieces of two different materials and subsequently coupled. Indeed, the catheter tube 108 includes a first section 118 including the tip 114, a second section 120 including the side aperture 116, and an optional transition section 122 therebetween depending upon the manner in which the first section 118 and the second section 120 of the catheter tube 108 are coupled. For example, the first and second sections 118 and 120 of the catheter tube 108 can be bonded by heat, solvent, or adhesive such that the first and second sections 118 and 120 abut each other, or the second section 120 can be inserted into the first section 118 and bonded thereto by heat, solvent, or adhesive, thereby forming the transition section 122. Advantageously, the latter coupling of inserting the second section 120 into the first section 118 facilitates incorporation of a smooth taper into the transition section 122, which taper is useful for dilation during methods of using the RICC assembly 100.

The first section 118 of the catheter tube 108 can be formed of a first material (e.g., a polymeric material such as polytetrafluoroethylene, polypropylene, or polyurethane) having a first durometer, while the second section 120 of the catheter tube 108 can be formed of a second material (e.g., a polymeric material such as polyvinyl chloride, polyethylene, polyurethane, or silicone) having a second durometer less than the first durometer. For example, each section of the first section 118 and the second section 120 of the catheter tube 108 can be made from a different polyurethane having a different durometer. Indeed, polyurethane is advantageous in that polyurethane sections of the catheter tube 108 can be relatively rigid at room-temperature but become more flexible in vivo at body temperature, which reduces irritation to vessel walls and phlebitis. Polyurethane is also advantageous in that can be less thrombogenic than some other polymers.

The catheter tube 108 having at least the first section 118 of the first polymeric material and the second section 120 of the second polymeric material has a column strength sufficient to prevent buckling of the catheter tube 108 when the catheter tube 108 is inserted into an insertion site and advanced through a vasculature of a patient. The column strength of the catheter tube 108 is notable in that it makes it possible to rapidly insert the catheter tube 108 into the insertion site and advance the catheter tube 108 through the vasculature of the patient without using the Seldinger technique.

It should be understood the first durometer and the second durometer can be on different scales (e.g., Type A or Type D), so the second durometer of the second polymeric material might not be numerically less than the first durometer of the first polymeric material. That said, the hardness of the second polymeric material can still be less than the hardness of the first polymeric material as the different scales—each of which ranges from 0 to 100—are designed for characterizing different materials in groups of the materials having a like hardness.

Notwithstanding the foregoing, the first section 118 and the second section 120 of the catheter tube 108 can be formed of a same polymeric material or different polymeric materials having substantially equal durometers provided a column strength of the catheter tube 108 is sufficient to prevent buckling of the catheter tube 108 when inserted into an insertion site and advanced through a vasculature of a patient.

The one-or-more catheter-tube lumens can extend through an entirety of the catheter tube 108; however, only one catheter-tube lumen typically extends from a proximal end of the catheter tube 108 to a distal end of the catheter tube 108 in a multiluminal RICC (e.g., a diluminal RICC, a triluminal RICC, a tetraluminal RICC, a pentaluminal RICC, a hexaluminal RICC, etc.). Indeed, the tip 114 typically includes a single lumen therethrough. Optionally, the single lumen through the tip 114 can be referred to as a "tip lumen," particularly in reference to the first section 118 of the catheter tube 108, which is formed separately from a remainder of the catheter tube 108 and coupled thereto.

Again, the side aperture 116 is through a side of the catheter tube 108 in the distal-end portion of the catheter tube 108; however, the side aperture 116 is proximal of the first section 118 of the catheter tube 108. The side aperture 116 opens into an introducing lumen 124 of the one-or-more catheter-tube lumens. The introducing lumen 124 extends from at least the side aperture 116 in the second section 120 of the catheter tube 108, through the first section 118 of the catheter tube 108 distal thereof, and to a distal end of the RICC 102 (e.g., the distal end of the catheter tube 108 or a distal end of the tip 114). The introducing lumen 124 is coincident with a distal-end portion of the one catheter-tube lumen set forth above that typically extends from the proximal end of the catheter tube 108 to the distal end of the catheter tube 108, particularly the distal-end portion of the foregoing catheter-tube lumen distal of the side aperture 116.

The catheter hub 110 is coupled to a proximal-end portion of the catheter tube 108. The catheter hub 110 includes one or more catheter-hub lumens corresponding in number to the one-or-more catheter-tube lumens. The one-or-more catheter-hub lumens extend through an entirety of the catheter hub 110 from a proximal end of the catheter hub 110 to a distal end of the catheter hub 110.

Each extension leg of the one-or-more extension legs 112 is coupled to the catheter hub 110 by a distal-end portion thereof. The one-or-more extension legs 112 respectively include one or more extension-leg lumens, which, in turn, correspond in number to the one-or-more catheter-tube lumens. Each extension-leg lumen of the one-or-more extension-leg lumens extends through an entirety of the extension leg from a proximal end of the extension leg to a distal end of the extension leg.

Each extension leg of the one-or-more extension legs 112 typically includes a Luer connector coupled to the extension leg, through which Luer connector the extension leg and the extension-leg lumen thereof can be connected to another medical device.

While the RICC 102 can be a monoluminal or multiluminal RICC (e.g., a diluminal RICC, a triluminal RICC, a tetraluminal RICC, a pentaluminal RICC, a hexaluminal RICC, etc.), the RICC 102 shown in FIGS. 1-12 is triluminal including a set of three lumens. The set of three lumens includes, for example, a distal lumen 126, a medial lumen 128, and a proximal lumen 130 formed of fluidly connected portions of three catheter-tube lumens, three hub lumens, and three extension-leg lumens. Whether the RICC 102 is monoluminal or multiluminal, the RICC 102 includes at least the distal lumen 126. The distal lumen 126 includes at least the one catheter-tube lumen set forth above that typically extends from the proximal end of the catheter tube 108 to the distal end of the catheter tube 108 as a catheter tube-lumen portion of the distal lumen 126, as well as a fluidly connected hub- and extension leg-lumen portions of the distal lumen 126. In accordance with the foregoing catheter-tube lumen, the introducing lumen 124 of the catheter tube 108 is coincident with a distal-end portion of the distal lumen 126, particularly the distal-end portion of the distal lumen 126 distal of the side aperture 116. In addition, the distal lumen 126 has a distal-lumen aperture 132 in the distal end of the RICC 102 (e.g., the distal end of the catheter tube 108 or the distal end of the tip 114). The medial lumen 128 has a medial-lumen aperture 134 in the side of the catheter tube 108 proximal of the distal-lumen aperture 132 and distal of the following proximal-lumen aperture 136 such that the medial lumen 128 is between the distal-lumen aperture 132 and the proximal-lumen aperture 136. The proximal lumen 130 has a proximal-lumen aperture 136 in the side of the catheter tube 108 proximal of the medial-lumen aperture 134. The side aperture 116 of the catheter tube 108 can be between the distal-lumen aperture 132 and the medial-lumen aperture 134, between the medial-lumen aperture 134 and the proximal-lumen aperture 136, or proximal of the proximal-lumen aperture 136 as shown in FIG. 9 such that each lumen aperture of the distal-lumen aperture 132, the medial-lumen aperture 134, and the proximal-lumen aperture 136 is distal of the side aperture 116.

The RICC 102 can further include a maneuver guidewire 138. While not shown, the maneuver guidewire 138 can include an atraumatic tip (e.g., a coiled or partially coiled tip) and a length sufficient for advancing the maneuver guidewire 138 to the lower ⅓ of the superior vena cava ("SVC") of the heart. The maneuver guidewire 138 can be captively disposed in the RICC 102 in at least a ready-to-deploy state of the RICC assembly 100. For example, the maneuver guidewire 138 can be disposed in the distal lumen 126 of the RICC 102 with a proximal-end portion or a medial portion of the maneuver guidewire 138 disposed in the extension leg-lumen portion of the distal lumen 126, the medial portion or a distal-end portion of the maneuver guidewire 138 disposed in the hub-lumen portion of the distal lumen 126, and the distal-end portion of the maneuver guidewire 138 disposed in the catheter tube-lumen portion of the distal lumen 126, which is formed of the one catheter-tube lumen set forth above that typically extends from the proximal end of the catheter tube 108 to the distal end of the catheter tube 108. However, the distal-end portion of the foregoing catheter-tube lumen distal of the side aperture 116 is coincident with the introducing lumen 124, which, as set forth below, is occupied by the introducer needle 143 in at least the ready-to-deploy state of the RICC assembly 100. Due to the presence of the introducer needle 143 in the introducing lumen 124, a distal end of the maneuver guidewire 138 is just short of the side aperture 116 in at least the ready-to-deploy state of the RICC assembly 100.

The maneuver guidewire 138 includes a stop 140 (e.g., a hub, a ball, a slug, etc.) about a proximal-end portion of the maneuver guidewire 138 forming a stop end (e.g., a hub end, a ball end, a slug end, etc.) of the maneuver guidewire 138. The stop end of the maneuver guidewire 138 is larger than a proximal-end opening of the distal lumen 126 or the extension leg-lumen portion thereof, thereby providing a distal limit for advancing the maneuver guidewire 138 into the RICC 102. In addition, the maneuver guidewire 138 is disposed in a fixed-length sterile barrier 142 (e.g., a longitudinal bag) including a closed or sealed proximal end and an otherwise open distal end removably coupled (e.g., removably adhered) to a proximal end of the Luer connector of the extension leg for manual removal of both the sterile barrier 142 and the maneuver guidewire 138 when needed.

A combination of the fixed length of the sterile barrier 142, the closed or sealed proximal end of the sterile barrier 142, and the distal end of the sterile barrier 142 coupled to the Luer connector provides a limited tract within which the maneuver guidewire 138 can proximally move, thereby providing a proximal limit for withdrawing the maneuver guidewire 138 from the RICC 102. The proximal limit keeps the atraumatic tip of the maneuver guidewire 138 in the distal lumen 126 where, in at least the embodiment of the atraumatic tip having the coiled or partially coiled tip, the atraumatic tip remains in a straightened or uncoiled state. This is advantageous for it can be particularly difficult to reinsert such a guidewire in a lumen of a medical device such as a catheter. Optionally, the stop end of the maneuver guidewire 138 is coupled (e.g., adhered) to the proximal end of the sterile barrier 142 to maintain the stop end of the maneuver guidewire 138 in the proximal end of the sterile barrier 142, thereby reducing a mismatch between a length of the proximal-end portion of the maneuver guidewire 138 extending beyond the proximal end of the RICC 102 (e.g., a proximal end of the Luer connector) and an unpleated length of the sterile barrier 142. Reducing the mismatch between the foregoing lengths reduces a likelihood of losing the stop end of the maneuver guidewire 138 in a medial portion of the sterile barrier 142, which could require time and effort to rematch that would be better spent focusing on the patient.

In addition to providing the proximal limit for withdrawing the maneuver guidewire from the RICC 102, the sterile barrier 142 is configured to maintain sterility of the maneuver guidewire 138 both before use (e.g., shipping and handling, storage, etc.) of the RICC assembly 100 and during use of the RICC assembly 100. During use of the RICC assembly 100, the sterile barrier 142 is configured to provide a no-touch advancing means for advancing the maneuver guidewire 138 into a blood-vessel lumen of a patient upon establishing a needle tract thereto. Likewise, the sterile barrier 142 is configured to provide a no-touch withdrawing means for withdrawing the maneuver guidewire 138 from the blood-vessel lumen of the patient, for example, after the catheter tube 108 has been advanced over the maneuver guidewire 138.

While not shown, the RICC 102 can further include stiffening stylets such as a stylet in either lumen or both lumens of the medial lumen and the proximal lumen of the triluminal embodiment of the RICC 102 for stiffening the RICC 102, thereby providing additional column strength to prevent buckling of the catheter tube 108 when the catheter tube 108 is inserted into an insertion site and advanced through a vasculature of a patient.

The introducer 104 includes an introducer needle 143, a syringe 144 operably connected to the introducer needle 143, and an access guidewire 146 captively disposed in the introducer 104. The introducer 104 can further include a fluid-pressure indicator 148 operably connected to the introducer needle 143.

The introducer needle 143 includes a needle hub 150 and a cannula 152 extending from the needle hub 150. The needle hub 150 is translucent and preferably colorless for observing blood flashback from a venipuncture with the cannula 152. When the RICC assembly 100 is in at least the ready-to-deploy state as shown in FIGS. 1-7, little more than a cannula tip 154 (e.g., a beveled tip) of the cannula 152 extends from the distal end of the RICC 102 for the venipuncture with the cannula 152. Indeed, a distal-end portion (e.g., about 7 cm) of the cannula 152 extends through the longitudinal through hole of the distal coupler of the coupling system 106 set forth below, through the side aperture 116 of the catheter tube 108, along the introducing lumen 124 of the catheter tube 108, and through the distal end of the RICC 102 when the RICC assembly 100 is in at least the ready-to-deploy state thereof. However, in some embodiments, 2-3 cm or more of the distal-end portion of the cannula 152 can extend from the distal end of the RICC 102 for the venipuncture with the cannula 152. In such embodiments, the first section 118 of the catheter tube 108 is shorter in length as opposed to the cannula 152 being longer in length.

When present, the fluid-pressure indicator 148 extends from a side arm 156 of the needle hub 150. The fluid-pressure indicator 148 includes a closed end and an open end fluidly coupled to a needle lumen of the introducer needle 143 by way of a side-arm lumen of the side arm 156. The fluid-pressure indicator 148 is configured as a built-in accidental arterial indicator, wherein blood under sufficient pressure (e.g., arterial blood) can enter the fluid-pressure indicator 148 and compress a column of air within the fluid-pressure indicator 148. However, it is also possible to observe the blood flashback from the venipuncture with the cannula 152 in the fluid-pressure indicator 148. That said, the blood flashback form is normally observed in the needle hub 150, the side arm 156 of the needle hub 150, or the syringe 144.

The syringe 144 includes a barrel 158, a plunger 160 disposed in the barrel 158, and a syringe tip 162 extending from a distal end of the barrel 158, which is coupled to the needle hub 150 of the introducer needle 143 when the RICC assembly 100 is in at least the ready-to-deploy thereof. The syringe 144 also includes a syringe portion of an access-guidewire lumen 164 formed of fluidly connected portions of a plunger lumen of the plunger 160, a syringe-tip lumen of the syringe tip 162, and any space within the barrel 158 formed by pulling the plunger 160 partially out of the barrel 158 such as in an operating state of a number of operating states of the RICC assembly 100 (e.g., during the blood-aspirating step of the method set forth below). Another portion of the access-guidewire lumen 164 is the introducer-needle portion of the access-guidewire lumen 164, namely the needle lumen of the introducer needle 143, particularly when the introducer needle 143 is operably connected to the syringe 144 as in most states of the RICC assembly 100.

The plunger 160 includes a sealing mechanism in a proximal-end portion of the plunger 160 for sealing off the access-guidewire lumen 164. The sealing mechanism is configured to seal off the access-guidewire lumen 164 to prevent blood from discharging (e.g., flashing back) through a proximal end of the plunger 160 during a venipuncture or while withdrawing the access guidewire 146 from a blood-vessel lumen of a patient, thereby minimizing or preventing a potential for contaminating an operating field or any clinicians operating within the operating field. Notwithstanding the sealing mechanism, the access guidewire 146 is also disposed in the sterile barrier 170 set forth below, which complements the sealing mechanism in minimizing or preventing the potential for contaminating the operating field or any clinicians operating within the operating field.

As shown in FIG. 8, the sealing mechanism can be a cartridge 166 disposed in a cavity in a distal-end portion of a main body of the plunger 160 and held in the cavity by a flanged end piece of the plunger 160. The cartridge 166 is coaxially aligned with the access-guidewire lumen 164 or the plunger-lumen portion thereof such that an unwrapped, bare-wire portion the access guidewire 146 passes through proximal- and distal-end through holes of the cartridge 166, which have inner diameters commensurate with an outer diameter of the access guidewire 146. Optionally, the sealing mechanism includes one or more gaskets such as 'O'-rings within the cartridge 166 or as an alternative to the cartridge 166. Instead of the cartridge 166, for example, the one-or-more 'O'-rings can be axially compressed in the cavity by the flanged end piece of the plunger 160, which, in turn, radially compresses the 'O'-rings around the access guidewire 146, thereby sealing off the access-guidewire lumen 164.

The access guidewire 146 is captively disposed in the introducer 104 such that at least a portion of the access guidewire 146 is always in a portion (e.g., the plunger-lumen portion, the needle-lumen portion, etc.) of the access-guidewire lumen 164 no matter the state of the RICC assembly 100. For example, when the access guidewire 146 is withdrawn to its proximal limit, a distal-end portion of the access guidewire 146 is disposed in at least a distal-end portion of the plunger lumen. Meanwhile, a proximal-end portion of the access guidewire 146 extends through or beyond a proximal end of the introducer 104 (e.g., a proximal end of the plunger 160). When the RICC assembly 100 is in at least the ready-to-deploy state thereof with a distal end of the access guidewire 146 just short of the cannula tip 154, a medial portion of the access guidewire 146 is disposed between the distal-end portion of the plunger lumen and a proximal-end portion of the needle lumen. And when the access guidewire 146 is advanced to its distal limit in some operating states of the number of operating states of the RICC assembly 100 (e.g., during the access guidewire-advancing step of the method set forth below), the proximal-end portion of the access guidewire 146 is disposed in at least a proximal-end portion of the plunger lumen. Meanwhile, a result of its sufficient length, the distal-end portion of the access guidewire 146 extends through or beyond the distal end of the RICC 102 (e.g., the distal end of the catheter tube 108 or a distal end of the tip 114).

The access guidewire 146 includes a stop 168 (e.g., a hub, a ball, a slug, etc.) about a proximal-end portion of the access guidewire 146 forming a stop end (e.g., a hub end, a ball end, a slug end, etc.) of the access guidewire 146. The stop end of the access guidewire 146 is larger than a proximal-end opening of the access-guidewire lumen 164 or the plunger lumen thereof, thereby providing the foregoing distal limit for advancing the access guidewire 146 into the introducer 104. In addition, the access guidewire 146 is disposed in a fixed-length sterile barrier 170 (e.g., a longitudinal bag) including a closed or sealed proximal end and an otherwise open distal end coupled (e.g., adhered) to the proximal end of the plunger 160. A combination of the fixed length of the sterile barrier 170, the closed or sealed proximal end of the sterile barrier 170, and the distal end of the sterile barrier 170 coupled to the plunger 160 provides a limited tract within which the access guidewire 146 can proximally move, thereby providing the foregoing proximal limit for withdrawing the access guidewire 146 from the introducer 104. Optionally, the stop end of the access guidewire 146 is coupled (e.g., adhered) to the proximal end of the sterile barrier 170 to maintain the stop end of the access guidewire 146 in the proximal end of the sterile barrier 170, thereby reducing a mismatch between a length of the proximal-end portion of the access guidewire 146 extending beyond the proximal end of the introducer 104 (e.g., the proximal end of the plunger 160) and an unpleated length of the sterile barrier 170. Reducing the mismatch between the foregoing lengths reduces a likelihood of losing the stop end of the access guidewire 146 in a medial portion of the sterile barrier 170, which could require time and effort to rematch that would be better spent focusing on the patient.

In addition to providing the proximal limit for withdrawing the access guidewire 146 from the introducer 104, the sterile barrier 170 is configured to maintain sterility of the access guidewire 146 both before use (e.g., shipping and handling, storage, etc.) of the RICC assembly 100 and during use of the RICC assembly 100. During use of the RICC assembly 100, the sterile barrier 170 is configured to provide a no-touch advancing means for advancing the access guidewire 146 into a blood-vessel lumen of a patient upon establishing a needle tract thereto. Likewise, the sterile barrier 170 is configured to provide a no-touch withdrawing means for withdrawing the access guidewire 146 from the blood-vessel lumen of the patient, for example, after the catheter tube 108 has been advanced over the access guidewire 146. Furthermore, as set forth above, the sterile barrier 170 complements the sealing mechanism in minimizing or preventing the potential for blood contaminating the operating field or any clinicians operating within the operating field. Indeed, the sterile barrier 170 is configured as secondary containment for any blood that might discharge (e.g., flash back) through the proximal end of the plunger 160 during a venipuncture or while withdrawing the access guidewire 146 from the blood-vessel lumen of the patient should the sealing mechanism fail in any way to prevent blood from discharging through the proximal end of the plunger 160.

The coupling system 106 includes a distal coupler 172 and a proximal coupler 174 configured to couple the RICC 102 and the introducer 104 together by corresponding proximal-end and distal-end portions thereof in at least the ready-to-deploy state of the RICC assembly 100 while allowing the introducer 104 to slide relative to the RICC 102 (or vice versa).

The distal coupler 172 includes a catheter-tube clip configured to both slidably and removably attach to the catheter tube 108 proximal of the side aperture 116. The distal coupler 172 also includes a longitudinal through hole and a tab 176 in a distal-end portion of the distal coupler 172. The cannula 152 of the introducer needle 143 extends through the longitudinal through hole of the distal coupler 172, through the side aperture 116 of the catheter tube 108, along the introducing lumen 124 of the catheter tube 108, and through the distal end of the RICC 102 when the RICC assembly 100 is in at least the ready-to-deploy state thereof. The tab 176 is configured to allow a clinician to single handedly advance the RICC 102 off the cannula 152 with a single finger of a hand (e.g., with a flick-type motion of the finger) while holding the introducer 104 (e.g., by the distal-end portion of the barrel 158 of the syringe 144 including the syringe clip 180 as set forth below) between a thumb and another finger or fingers of the same hand, thereby providing a no-touch mechanism for advancing the RICC 102, specifically the distal-end portion of the catheter tube 108, over the cannula 152 and into a blood-vessel lumen of a patient.

The proximal coupler 174 includes a catheter-hub clip 178 configured to both slidably and removably attach to the catheter hub 110 or the one-or-more extension legs 112 and a syringe clip 180 configured to removably attach to the syringe 144. The catheter-hub clip 178 is configured for suspending the RICC 102 by the catheter hub 110 in at least the ready-to-deploy state of the RICC assembly 100, thereby keeping the RICC 102 from drooping. The catheter-hub clip 178 is also configured for suspending the RICC 102 by the one-or-more extension legs 112 in some operating states of the number of operating states of the RICC assembly 100 (e.g., during the introducer-removing step of the method set forth below), thereby further keeping the RICC 102 from drooping. The syringe clip 180 is configured to cradle the syringe 144 such that the syringe 144 rests in the syringe clip 180 by a distal-end portion of the barrel 158 in at least the ready-to-deploy state of the RICC assembly 100. Distal placement of the syringe clip 180 about the distal-end portion of the barrel 158 of the syringe 144 encourages holding or handling the introducer 104 in a location that provides better control of a distal-end portion of the RICC 102 including the cannula tip 154 of the cannula 152, for example, when establishing a needle tract from an area of skin to a blood-vessel lumen of a patient. The syringe clip 180 can include a gripping portion (e.g., a pattern of bumps, through holes, etc.) configured to facilitate gripping the syringe clip 180 for holding or handling the introducer 104.

The RICC 102 can further include a sterile barrier 182 (e.g., a collapsible or pleatable bag, a casing, etc.) configured to maintain sterility of the catheter tube 108 between the catheter hub 110 and the distal coupler 172 prior to insertion of the catheter tube 108 into a blood-vessel lumen of a patient. In at least the ready-to-deploy state of the RICC assembly 100, the sterile barrier 182 is over the catheter tube 108, between the catheter hub 110 about the proximal-end portion of the catheter tube 108 and the distal coupler 172, and coupled to the distal coupler 172. The sterile barrier 182 is configured to split apart when a sterile-barrier tab 184 of the sterile barrier 182 is removed from the catheter-hub clip 178 in which it is tucked and pulled away from the catheter tube 108, thereby providing a no-touch mechanism for removing the sterile barrier 182 from the catheter tube 108. The sterile barrier 182 has sufficient tensile strength to pull the distal coupler 172 off the catheter tube 108 without breaking when the sterile barrier 182 splits down to the distal coupler 172 while being pulled away from the catheter tube 108.

As set forth above, FIGS. 1-7 illustrate the RICC assembly 100 in at least the ready-to-deploy state thereof. While some operating states of the number of operating states of the RICC assembly 100 are also set forth above, additional operating states of the RICC assembly 100 can be discerned from steps of the method for inserting the RICC 102 set forth below.

Methods

A method of the RICC assembly 100 includes a method for inserting the RICC 102 into a blood-vessel lumen of a patient. Such a method includes, in some embodiments, a RICC assembly-obtaining step, a needle tract-establishing step, a first RICC-advancing step, and an introducer-withdrawing step.

The RICC assembly-obtaining step includes obtaining the RICC assembly 100. As set forth above, the RICC assembly 100 includes the RICC 102, the introducer 104 including the syringe 144 coupled to the introducer needle 143, and the coupling system 106 including the distal coupler 172 that couples the RICC 102 and the introducer 104 together by distal-end portions thereof in at least the ready-to-deploy state of the RICC assembly 100.

The method can further include a cannula tip-ensuring step of ensuring the cannula tip 154 extends from the distal end of the RICC 102 before the needle tract-establishing step. As set forth above, the cannula 152 extends through the longitudinal through hole of the distal coupler 172, through the side aperture 116 in the distal-end portion of the catheter tube 108, along the introducing lumen 124 of the catheter tube 108, and out the distal end of the RICC 102.

The needle tract-establishing step includes establishing a needle tract from an area of skin to the blood-vessel lumen of the patient with the cannula 152 of the introducer needle 143 while holding a distal-end portion of the barrel 158 of the syringe 144, for example, together with the syringe clip 180 of the proximal coupler 174 around the distal-end portion of the barrel 158. The needle tract-establishing step can also include ensuring blood flashes back into the needle hub 150 of the introducer needle 143, the side arm 156 of the needle hub 150, or the fluid-pressure indicator 148 extending from the side arm 156 of the needle hub 150.

The method can further include a blood-aspirating step. The blood-aspirating step includes aspirating blood with the syringe 144 before the access guidewire-advancing step set forth below or the introducer-withdrawing step. The blood-aspirating step confirms the cannula tip 154 is disposed in the blood-vessel lumen of the patient.

The method can further include an access guidewire-advancing step of advancing the access guidewire 146 into the blood-vessel lumen beyond a distal end of the cannula 152 (e.g., the cannula tip 154) before the first RICC-advancing step. As set forth above, the access guidewire 146 is disposed in the access-guidewire lumen 164 formed of at least the plunger lumen 160 of the syringe 144 and the needle lumen of the introducer needle 143, which facilitates first-stick success by making the access guidewire 146 immediately available before the blood-lumen vessel can be lost due to small inadvertent movements. The access guidewire-advancing step should be performed before the first RICC-advancing step such that the distal-end portion of the catheter tube 108 can be advanced over the access guidewire 146 as well.

The first RICC-advancing step includes advancing the distal-end portion of the catheter tube 108 into the blood-vessel lumen over the cannula 152, the access guidewire 146, or both. As set forth above, the catheter tube 108 includes the first section 118 formed of the first material having the first durometer and the second section 120 formed of the second material having the second durometer less than the first durometer. The first section 118 of the catheter tube 108 is configured with a column strength for advancing the catheter tube 108 into the blood-vessel lumen over the access guidewire 146 or the maneuver guidewire 138 after the maneuver guidewire-advancing step set forth below. For example, the first RICC-advancing step can include advancing the catheter tube 108 into the blood-vessel lumen with a single finger of a hand (e.g., with a flick-type motion of the finger) while holding the barrel 158 of the syringe 144 by the syringe clip 180 between a thumb and another finger or fingers of the same hand. The distal coupler 172 includes the tab 176 configured for advancing the catheter tube 108 into the blood-vessel lumen with the single finger.

The first catheter-advancing step can also include advancing the catheter hub 110 of the RICC 102 from the catheter-hub clip 178 of the proximal coupler 174. After advancing the catheter hub 110 from the catheter-hub clip 178, the one-or-more extension legs 112 of the RICC 102 are advanced within the catheter-hub clip 178 in accordance with the first catheter-advancing step. The RICC 102 is configured to suspend from the coupling system 106 until at least withdrawing the cannula 152 from both the introducing lumen 124 and the longitudinal through hole of the distal coupler 172 such as after the introducer-removing step set forth below.

The method can further include an access guidewire-withdrawing step of withdrawing the access guidewire 146 from the blood-vessel lumen of the patient such as by the stop end of the access guidewire 146. The access guidewire-withdrawing step can be performed after the first catheter-advancing step such as after the distal-end portion of the catheter tube 108 is suitably placed within the blood-vessel lumen over both the cannula 152 and the access guidewire 146.

The introducer-withdrawing step includes withdrawing the cannula 152 from the introducing lumen 124 by way of the side aperture 116 of the catheter tube 108. Like the access guidewire-withdrawing step, the introducer-withdrawing step can be performed after the first catheter-advancing step such as after the distal-end portion of the catheter tube 108 is suitably placed within the blood-vessel lumen over both the cannula 152 and the access guidewire 146.

The method can further include an introducer-removing step of completely removing the introducer 104 from the RICC assembly 100 after the introducer-withdrawing step. The introducer-removing step includes withdrawing the cannula 152 from the longitudinal through hole of the distal coupler 172 while proximally sliding the catheter-hub clip 178 along the one-or-more extension legs 112. Upon withdrawing the cannula 152 from the longitudinal through hole of the distal coupler 172, each extension leg of the one-or-more extension legs 112 can be removed through an opening in the catheter-hub clip 178, which opening is commensurate with or slightly wider in diameter than that of any extension leg.

The method can further include a maneuver guidewire-advancing step of advancing the maneuver guidewire 138 into the blood-vessel lumen by way of, for example, the distal-lumen aperture 132 in the distal end of the RICC 102. As set forth above, the introducing lumen 124 of the catheter tube 108 is coincident with the distal-end portion of the distal lumen 126, particularly the distal-end portion of the distal lumen 126 distal of the side aperture 116. As such, the introducer-removing step of completely removing the introducer 104 from the RICC assembly 100 should be performed before the maneuver guidewire-advancing step to ensure the distal lumen 126, or the introducing lumen 124 thereof, is free of both the cannula 152 and the access guidewire 146.

The method can further include a second RICC-advancing step of advancing the distal-end portion of the catheter tube 108 farther into the blood-vessel lumen over the maneuver guidewire 138 such as to the SVC. The maneuver guidewire 138 provides the second section 120 of the catheter tube 108 columnar strength for the second RICC-advancing step. Concomitantly, the second catheter-advancing step includes sliding the distal coupler 172 proximally towards the catheter hub 110 to uncover the catheter tube 108. As set forth above, the catheter tube 108 is covered by the sterile barrier 182 between the catheter hub 110 about the proximal-end portion of the catheter tube 108 and the distal coupler 172 in at least the ready-to-deploy state of the RICC assembly 100.

The method can further include a sterile barrier-removing step of removing the sterile barrier 182 and a remainder of the coupling system 106 from the RICC 102. The sterile barrier-removing step includes removing the sterile barrier 182 and the distal coupler 172 from the RICC 102 by pulling the sterile-barrier tab 184 of the sterile barrier 182 opposite the distal coupler 172 away from the catheter tube 108 to split the sterile barrier 182 apart along its length, then pulling the distal coupler 172 from the catheter tube 108 by the sterile barrier 182 to which the distal coupler 172 is slidably attached.

The method can further include a maneuver guidewire-withdrawing step of withdrawing the maneuver guidewire 138 from the blood-vessel lumen of the patient, as well as withdrawing the maneuver guidewire 138 from the RICC 102.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A rapidly insertable central catheter ("RICC") assembly, comprising:
    a RICC including:
        a catheter tube including:
            a first section formed of a first material having a first durometer;
            a second section formed of a second material having a second durometer less than the first durometer; and
            a side aperture through a side of the catheter tube in a distal-end portion thereof but proximal of the first section of the catheter tube, the side aperture opening into an introducing lumen of the catheter tube that extends from at least the side aperture to a distal end of the RICC;
        a catheter hub coupled to a proximal-end portion of the catheter tube; and
        one or more extension legs, each extension leg of the one or more extension legs coupled to the catheter hub by the distal-end portion thereof;
    an introducer including:
        an introducer needle having a cannula extending through the distal end of the RICC when the RICC assembly is in at least a ready-to-deploy state of the RICC assembly; and
        a syringe having a syringe tip coupled to a needle hub of the introducer needle; and
    a coupling system configured to couple the RICC and the introducer together, the coupling system including:
        a distal coupler slidably attached to the catheter tube proximal of the side aperture; and
        a proximal coupler slidably attached to the catheter hub and removably attached to the syringe in the ready-to-deploy state of the RICC assembly, the coupling system configured to allow the RICC to slide relative to the introducer.

2. The RICC assembly of claim 1, wherein the cannula further extends through a longitudinal through hole of the distal coupler, through the side aperture of the catheter tube, and along the introducing lumen of the catheter tube before exiting through the distal end of the RICC when the RICC assembly is in at least the ready-to-deploy state thereof.

3. The RICC assembly of claim 1, the distal coupler including a tab configured to allow a clinician to single handedly advance the RICC off the cannula with a single finger of a hand while holding the introducer between a thumb and another finger or fingers of the hand.

4. The RICC assembly of claim 1, the introducer further including:
    an access guidewire disposed in an access-guidewire lumen formed of at least a plunger lumen of a plunger of the syringe and a needle lumen of the introducer needle, the access guidewire having a length sufficient for extension of the access guidewire through the distal end of the RICC.

5. The RICC assembly of claim 4, wherein the plunger includes a sealing mechanism in a proximal-end portion of the plunger for sealing off the access-guidewire lumen, the sealing mechanism configured to prevent blood from discharging through a proximal end of the plunger during a venipuncture or while withdrawing the access guidewire from a blood-vessel lumen of a patient.

6. The RICC assembly of claim 5, wherein the access guidewire is captively disposed in the introducer by a stop about a proximal-end portion of the access guidewire and a closed end of an access-guidewire sterile barrier of a fixed length coupled to the proximal end of the plunger, the stop providing a distal limit to advancing the access guidewire and the closed end of the access-guidewire sterile barrier around the access guidewire providing a proximal limit to withdrawing the access guidewire.

7. The RICC assembly of claim 4, the introducer further including a fluid-pressure indicator extending from a side arm of the needle hub, the fluid-pressure indicator fluidly coupled to the needle lumen of the introducer needle by way of a side-arm lumen of the side arm for observing blood flashback.

8. The RICC assembly of claim 4, wherein the proximal coupler includes a catheter-hub clip from which the RICC is configured to suspend by the catheter hub in at least the ready-to-deploy state of the RICC assembly or the one or more extension legs when the proximal coupler is advanced thereover in an operating state of the RICC assembly.

9. The RICC assembly of claim 8, wherein the proximal coupler includes a syringe clip within which the introducer is configured to rest by a distal-end portion of a barrel of the syringe in at least the ready-to-deploy state of the RICC assembly.

10. The RICC assembly of claim 9, the RICC further including a collapsible catheter-tube sterile barrier over the catheter tube between the catheter hub and the distal coupler to which the collapsible catheter-tube sterile barrier is coupled, the collapsible catheter-tube sterile barrier configured to split apart when a sterile-barrier tab of the collapsible catheter-tube sterile barrier is removed from the catheter-hub clip and the collapsible catheter-tube sterile barrier is pulled away from the catheter tube by the sterile-barrier tab.

11. The RICC assembly of claim 10, wherein the collapsible catheter-tube sterile barrier has sufficient tensile strength to pull the distal coupler off the catheter tube without breaking when the collapsible catheter-tube sterile barrier splits down to the distal coupler while being pulled away from the catheter tube.

12. The RICC assembly of claim 1, wherein the RICC includes a set of three lumens including a distal lumen, a medial lumen, and a proximal lumen formed of fluidly connected portions of three catheter-tube lumens, three hub lumens, and three extension-leg lumens, the introducing lumen of the catheter tube coincident with a distal-end portion of the distal lumen.

13. The RICC assembly of claim 12, wherein the distal lumen has a distal-lumen aperture in a distal end of the RICC, the medial lumen has a medial-lumen aperture in the side of the catheter tube distal of the side aperture, and the proximal lumen has a proximal-lumen aperture in the side of the catheter tube distal of the side aperture but proximal of the medial-lumen aperture.

14. The RICC assembly of claim 1, the RICC further including a maneuver guidewire disposed in the distal lumen having a length sufficient for extension of the maneuver guidewire to a lower ⅓ of a superior vena cava of a heart, the maneuver guidewire captively disposed in the RICC by a stop about a proximal-end portion of the maneuver guidewire and a closed end of a maneuver-guidewire sterile barrier of a fixed length coupled to a Luer connector, the stop providing a distal limit to advancing the maneuver guidewire and the closed end of the maneuver-guidewire sterile barrier around the maneuver guidewire providing a proximal limit to withdrawing the maneuver guidewire.

15. A rapidly insertable central catheter ("RICC") assembly, comprising:
    a RICC including:
        a catheter tube including a side aperture through a side of the catheter tube in a distal-end portion thereof, the side aperture opening into an introducing lumen of the catheter tube that extends from at least the side aperture to a distal end of the RICC; and
        a catheter hub coupled to a proximal-end portion of the catheter tube;
    an introducer including:
        an introducer needle having a cannula extending through the distal end of the RICC when the RICC assembly is in at least a ready-to-deploy state of the RICC assembly; and
        a syringe having a syringe tip coupled to a needle hub of the introducer needle; and
    a coupling system configured to couple the RICC and the introducer together, the coupling system including:
        a distal coupler slidably attached to the catheter tube proximal of the side aperture; and
        a proximal coupler slidably attached to the catheter hub and removably attached to the syringe in the ready-to-deploy state of the RICC assembly, the coupling system configured to allow the RICC to slide relative to the introducer.

16. The RICC assembly of claim 15, wherein the cannula further extends through a longitudinal through hole of the distal coupler, through the side aperture of the catheter tube, and along the introducing lumen of the catheter tube before exiting through the distal end of the RICC when the RICC assembly is in at least the ready-to-deploy state thereof, the distal coupler including a tab configured to allow a clinician to single handedly advance the RICC off the cannula with a single finger of a hand while holding the introducer between a thumb and another finger or fingers of the hand.

17. The RICC assembly of claim 15, the introducer further including:
    an access guidewire disposed in an access-guidewire lumen formed of at least a plunger lumen of a plunger of the syringe and a needle lumen of the introducer needle, the access guidewire having a length sufficient for extension of the access guidewire through the distal end of the RICC.

18. The RICC assembly of claim 17, wherein the plunger includes a sealing mechanism in a proximal-end portion of the plunger for sealing off the access-guidewire lumen, the sealing mechanism configured to prevent blood from discharging through a proximal end of the plunger during a venipuncture or while withdrawing the access guidewire from a blood-vessel lumen of a patient.

19. The RICC assembly of claim 18, wherein the access guidewire is captively disposed in the introducer by a stop about a proximal-end portion of the access guidewire and a closed end of an access-guidewire sterile barrier of a fixed length coupled to the proximal end of the plunger, the stop providing a distal limit to advancing the access guidewire and the closed end of the access-guidewire sterile barrier around the access guidewire providing a proximal limit to withdrawing the access guidewire.

20. The RICC assembly of claim 17, the introducer further including a fluid-pressure indicator extending from a side arm of the needle hub, the fluid-pressure indicator fluidly coupled to the needle lumen of the introducer needle by way of a side-arm lumen of the side arm for observing blood flashback.

21. The RICC assembly of claim 17, wherein the proximal coupler includes a catheter-hub clip from which the RICC is configured to suspend by the catheter hub in at least the ready-to-deploy state of the RICC assembly or one or more extension legs when the proximal coupler is advanced thereover in an operating state of the RICC assembly, each extension leg of the one or more extension legs coupled to the catheter hub by a distal-end portion thereof.

22. The RICC assembly of claim 21, wherein the proximal coupler includes a syringe clip within which the introducer is configured to rest by a distal-end portion of a barrel of the syringe in at least the ready-to-deploy state of the RICC assembly.

23. The RICC assembly of claim 21, the RICC further including a collapsible catheter-tube sterile barrier over the catheter tube between the catheter hub and the distal coupler to which the collapsible catheter-tube sterile barrier is coupled, the collapsible catheter-tube sterile barrier configured to split apart when a sterile-barrier tab of the collapsible catheter-tube sterile barrier is removed from the catheter-hub clip and the collapsible catheter-tube sterile barrier is pulled away from the catheter tube by the sterile-barrier tab.

24. The RICC assembly of claim 23, wherein the collapsible catheter-tube sterile barrier has sufficient tensile strength to pull the distal coupler off the catheter tube without breaking when the collapsible catheter-tube sterile barrier splits down to the distal coupler while being pulled away from the catheter tube.

25. The RICC assembly of claim 15, the RICC further including a maneuver guidewire disposed in the distal lumen having a length sufficient for extension of the maneuver guidewire to a lower ⅓ of a superior vena cava of a heart, the maneuver guidewire captively disposed in the RICC by a stop about a proximal-end portion of the maneuver guidewire and a closed end of a maneuver-guidewire sterile barrier of a fixed length coupled to a Luer connector, the stop providing a distal limit to advancing the maneuver guidewire and the closed end of the maneuver-guidewire sterile barrier around the maneuver guidewire providing a proximal limit to withdrawing the maneuver guidewire.

\* \* \* \* \*